(12) United States Patent
Walsh et al.

(10) Patent No.: US 9,108,947 B2
(45) Date of Patent: *Aug. 18, 2015

(54) INHIBITORS OF THE RENAL OUTER MEDULLARY POTASSIUM CHANNEL

(71) Applicant: Merck Sharp & Dohme Corp., Rahway, NJ (US)

(72) Inventors: Shawn P. Walsh, Bridgewater, NJ (US); Alexander Pasternak, Princeton, NJ (US); Zhi-Cai Shi, Monmouth Junction, NJ (US); Brian Cato, Secaucus, NJ (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/353,817

(22) PCT Filed: Oct. 25, 2012

(86) PCT No.: PCT/US2012/061890
§ 371 (c)(1),
(2) Date: Apr. 24, 2014

(87) PCT Pub. No.: WO2013/066717
PCT Pub. Date: May 10, 2013

(65) Prior Publication Data
US 2014/0275020 A1 Sep. 18, 2014

Related U.S. Application Data

(60) Provisional application No. 61/553,358, filed on Oct. 31, 2011.

(51) Int. Cl.
| | | |
|---|---|---|
| *C07D 307/88* | (2006.01) |
| *C07D 405/06* | (2006.01) |
| *C07D 405/14* | (2006.01) |
| *C07D 471/08* | (2006.01) |
| *C07D 487/04* | (2006.01) |

(52) U.S. Cl.
CPC ............ *C07D 405/06* (2013.01); *C07D 405/14* (2013.01); *C07D 471/08* (2013.01); *C07D 487/04* (2013.01)

(58) Field of Classification Search
CPC .................................................... C07D 307/88
See application file for complete search history.

(56) References Cited

U.S. PATENT DOCUMENTS

| | | |
|---|---|---|
| 2,988,551 A | 6/1961 | Morren |
| 3,435,002 A | 3/1969 | Holub |
| 3,632,608 A | 1/1972 | Holub |
| 3,749,722 A | 7/1973 | Holub |
| 4,579,863 A | 4/1986 | Horwell et al. |
| 4,806,536 A | 2/1989 | Cross et al. |
| 4,992,547 A | 2/1991 | Berner et al. |
| 5,145,885 A | 9/1992 | Berner et al. |
| 5,215,989 A | 6/1993 | Baldwin et al. |
| 5,614,526 A | 3/1997 | Godel et al. |
| 5,736,546 A | 4/1998 | Kawashima et al. |
| 6,150,356 A | 11/2000 | Lloyd et al. |
| 6,258,813 B1 | 7/2001 | Arlt et al. |
| 6,787,543 B2 | 9/2004 | Take et al. |
| 2004/0204404 A1 | 10/2004 | Zelle et al. |
| 2005/0215526 A1 | 9/2005 | Hulme et al. |
| 2005/0267121 A1 | 12/2005 | Li et al. |
| 2006/0183739 A1 | 8/2006 | Tsaklakidis et al. |
| 2006/0183742 A1 | 8/2006 | Mederski et al. |
| 2006/0211692 A1 | 9/2006 | Mederski et al. |
| 2007/0004750 A1 | 1/2007 | Lorsbach et al. |
| 2007/0093472 A1 | 4/2007 | Mederski et al. |
| 2008/0003214 A1 | 1/2008 | Cezanne et al. |
| 2010/0286123 A1 | 11/2010 | Pasternak et al. |

FOREIGN PATENT DOCUMENTS

| | | |
|---|---|---|
| EP | 0099148 B1 | 2/1988 |
| EP | 0175376 B1 | 4/1991 |
| EP | 1094063 A1 | 4/2001 |
| EP | 1939175 A1 | 7/2009 |
| FR | 2673182 | 8/1992 |
| FR | 2673182 A1 | 8/1992 |
| GB | 949088 A | 2/1964 |
| GB | 1575310 A | 9/1980 |
| GB | 2116967 | 7/1986 |
| JP | 10203986 | 8/1998 |

(Continued)

OTHER PUBLICATIONS

Walsh et al., caplus an 2013:427355.*
ACCF/AHA Practice Guideline, 2009 Focused update incorporated into the ACC/AHA 2005 guidelines . . . , Circulation, 2009, e391-e436, 119.
Baltzly, R., The preparation of N-mono-substituted and unsymmetrically disubstituted piperazines, J. Am. Chemoc., 1944, 263-266, 66.
Bhave, G., Small-molecule modulators of inward rectifier K+ channels: recent advances and future possibilities, Future Med Chem, 2010, 757-774, 2(5).
Bhave, G., Development of a selective small-molecule inhibitor Kir1.1, the renal outer medullary potassium channel, Mol. Pharmacol., 2011, 42-50, 79.

(Continued)

*Primary Examiner* — Sun Jae Yoo
(74) *Attorney, Agent, or Firm* — Nicole M. Beeler; Catherine D. Fitch

(57) ABSTRACT

This invention relates to compounds of Formula I having the following general structure:

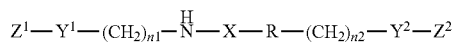

and pharmaceutically acceptable salts thereof which are inhibitors of the Renal Outer Medullary Potassium (ROMK) channel (Kir1.1). The compounds are useful as diuretics and natriuretics and therefore are useful for the therapy and prophylaxis of disorders resulting from excessive salt and water retention, including cardiovascular diseases such as hypertension and chronic and acute heart failure.

10 Claims, No Drawings

(56) References Cited

FOREIGN PATENT DOCUMENTS

| WO | 9744329 | | 11/1997 |
|---|---|---|---|
| WO | 0051611 | A1 | 9/2000 |
| WO | 0232874 | | 4/2002 |
| WO | 0204314 | A1 | 6/2002 |
| WO | 0250061 | A1 | 6/2002 |
| WO | 2004020422 | A1 | 3/2004 |
| WO | 2004037817 | A1 | 5/2004 |
| WO | 2004046110 | | 6/2004 |
| WO | 2005037843 | | 4/2005 |
| WO | 2005044797 | | 5/2005 |
| WO | 2006034341 | A2 | 3/2006 |
| WO | 2006034769 | A1 | 4/2006 |
| WO | 2006098342 | A1 | 9/2006 |
| WO | 2006129199 | A1 | 12/2006 |
| WO | 2007075629 | A2 | 7/2007 |
| WO | 2008147864 | | 12/2008 |
| WO | 2008147864 | A2 | 12/2008 |
| WO | 2009149508 | | 11/2009 |
| WO | 2010129379 | A1 | 11/2010 |
| WO | 2012058116 | A1 | 5/2012 |
| WO | 2012058134 | A1 | 5/2012 |
| WO | 2013028474 | A1 | 2/2013 |
| WO | 2013039802 | A1 | 3/2013 |
| WO | 2013062892 | A1 | 5/2013 |
| WO | 2013062900 | A1 | 5/2013 |
| WO | 2013066714 | A1 | 5/2013 |
| WO | 2013066718 | A2 | 5/2013 |
| WO | 2013090271 | A1 | 6/2013 |
| WO | 2014015495 | A1 | 1/2014 |
| WO | 2014018764 | A1 | 1/2014 |

OTHER PUBLICATIONS

Brater et al., Diuretic Therapy, Drug Therapy, 1998, 387-395, 339.
Brewster et al., Antihypertensive 1,4-bis (2-indol-3-ylethyl)piperazines, Chimie Ther., 1973, 169-172 (English trans.), 2.
Cerkvenik-Flajs V, Determination of residues of azaperone in the kidneys by liquid chromatography with fluorescence, Anal. Chim. Acta., 2007, 374-382, 586.
Chemical Abstracts (2004), Abstract No. 697771-49-6, "1,3-Isobenzofurandione 5-[[4-[(5-chloro-2-methoxyphenyl) sulfonyl]-1-...".
Cheymol et al., Increase in the effects of epinephrine and acetylcholine ..., Comptes Rendus des seances de la Societe de Biologie, 1951, 496-499 (English trans.), 145.
Fallen, K., The Kir channel immunoglobuling domain is essential for Kir1.1 (ROMK) thermodynamic stability, trafficing and gating, Channels, 2009, 57-66, 3.
Felker et al, Diuretic strategies in patients with acute decompensated heart failure, New Eng. J. Med., 2011, 797-805, 364.
Frank, Managing hypertension using combination therapy, Am. Fam. Physician, 2008, 1279-1286, 77.
International Search Report and Written Opinion for PCT/US2012/61890, mailed Jan. 11, 2013, 15 pages.
Kulkarni, YD, Possible antifertility agents, part III. Synthesis of 4-(substituted aminomethyl)-5,6,7-trimethoxy phthalid . . . (abstract)), Biol. Mem., 1987, 141-144, 13.
Lanyi et al., Piperazine-Derivatives II, Res. Lab. of Chinoin-Fabrik Chemisch-Pharma. Prod., 1968, 1431-1435 (English trans.), 18.
Lewis, L. M., High-throughput screening reveals a small-molecule inhibitor of the Renal Outer Medullary Potassium Channel and Kir7.1, Mol. Pharncol., 2009, 1094-1103, 76.
Lutz, R. E., Antimalarials. Some Piperazine Derivatives, J. Org. Chem., 1947, 771-775, 12, BO.
Miyake et al., Synthesis of 1-substituted isochroman . . . , Takeda Res. Lab., 1982, 24-40 (English trans.), 41.
Sica, D. A., Diuretic use in renal disease, Nature, 2012, 100-109, 8.
Zejc et al., Piperazine derivative of dimethylxanthines, Polish J. Pharmacol. & Pharm., 1975, 311-316 (English trans.), 27.
EP Search Report for 12845426.1 mailed Jun. 18, 2015; 6 pages.

* cited by examiner

INHIBITORS OF THE RENAL OUTER MEDULLARY POTASSIUM CHANNEL

CROSS REFERENCE TO RELATED APPLICATIONS

This application is a U.S. National Phase application under 35 U.S.C. §371 of PCT Application No. PCT/US12/061890 filed Oct. 25, 2012, which claims priority from U.S. Provisional Application Ser. No. 61/553,358, filed Oct. 31, 2011.

BACKGROUND OF THE INVENTION

The Renal Outer Medullary Potassium (ROMK) channel (Kir1.1) (see e.g., Ho, K., et al., *Cloning and expression of an inwardly rectifying ATP-regulated potassium channel*, Nature, 1993, 362(6415): p. 31-8.1, 2; and Shuck, M. E., et al., *Cloning and characterization of multiple forms of the human kidney ROM-K potassium channel*, J Biol Chem, 1994, 269(39): p. 24261-70) is a member of the inward rectifier family of potassium channels expressed in two regions of the kidney: thick ascending loop of Henle (TALH) and cortical collecting duct (CCD) (see Hebert, S. C., et al., *Molecular diversity and regulation of renal potassium channels*, Physiol Rev, 2005, 85(1): p. 319-713). At the TALH, ROMK participates in potassium recycling across the luminal membrane which is critical for the function of the Na$^+$/K$^+$/2Cl$^-$ co-transporter, the rate-determining step for salt reuptake in this part of the nephron. At the CCD, ROMK provides a pathway for potassium secretion that is tightly coupled to sodium uptake through the amiloride-sensitive sodium channel (see Reinalter, S. C., et al., *Pharmacotyping of hypokalaemic salt-losing tubular disorders*, Acta Physiol Scand, 2004, 181(4): p. 513-21; and Wang, W., *Renal potassium channels: recent developments*, Curr Opin Nephrol Hypertens, 2004, 13(5): p. 549-55). Selective inhibitors of the ROMK channel (also referred to herein as inhibitors of ROMK or ROMK inhibitors) are predicted to represent novel diuretics for the treatment of hypertension and other conditions where treatment with a diuretic would be beneficial with potentially reduced liabilities (i.e., hypo- or hyperkalemia, new onset of diabetes, dyslipidemia) over the currently used clinical agents (see Lifton, R. P., A. G. Gharavi, and D. S. Geller, *Molecular mechanisms of human hypertension*, Cell, 2001, 104(4): p. 545-56). Human genetics (Ji, W., et al., *Rare independent mutations in renal salt handling genes contribute to blood pressure variation*, Nat Genet, 2008, 40(5): p. 592-9; and Tobin, M. D., et al., *Common variants in genes underlying monogenic hypertension and hypotension and blood pressure in the general population*, Hypertension, 2008, 51(6): p. 1658-64) and genetic ablation of ROMK in rodents (see Lorenz, J. N., et al., *Impaired renal NaCl absorption in mice lacking the ROMK potassium channel, a model for type II Bartter's syndrome*, J Biol Chem, 2002, 277(40): p. 37871-80 and Lu, M., et al., *Absence of small conductance K+ channel (SK) activity in apical membranes of thick ascending limb and cortical collecting duct in ROMK (Bartter's) knockout mice*, J Biol Chem, 2002, 277(40): p. 37881-7) support these expectations. To our knowledge, the first small molecule selective inhibitors of ROMK were reported from work done at Vanderbilt University as described in Lewis, L. M., et al., *High-Throughput Screening Reveals a Small-Molecule Inhibitor of the Renal Outer Medullary Potassium Channel and Kir7.1*, Mol Pharmacol, 2009, 76(5): p. 1094-1103. However, continuing discovery of selective small molecule inhibitors of ROMK is still needed for the development of new treatments for hypertension and related disorders.

SUMMARY OF THE INVENTION

The present invention provides compounds of Formula I having the general structure below:

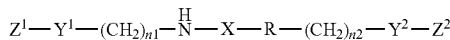

I where R represents a saturated 4-6-membered heterocyclic ring having 1 Nitrogen atom, and pharmaceutically acceptable salts thereof. The compounds of Formula I are inhibitors of the ROMK (Kir1.1) channel and can thus act as diuretics and natriuretics and are valuable pharmaceutically active compounds for the therapy and prophylaxis of diseases, including, but not limited to, cardiovascular diseases such as hypertension and conditions resulting from excessive salt and water retention. Methods of treatment comprising administering a therapeutically or prophylactically effective amount of a compound of Formula I to a patient in need of a diuretic and/or natriuretic agent are also provided. Compounds of Formula I can be used in combination with other therapeutically effective agents, including other drugs useful for the treatment of hypertension and conditions resulting from excessive salt and water retention. The invention furthermore relates to processes for preparing compounds of Formula I, and pharmaceutical compositions which comprise any of the compounds of Formula I.

DETAILED DESCRIPTION OF THE INVENTION

The present invention provides compounds of Formula I having the structure below:

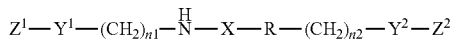

I and pharmaceutically acceptable salts thereof wherein:
—X—R—(CH$_2$)n2- is

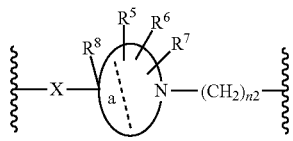

and where R represents a 4-6-membered heterocyclic ring having 1 Nitrogen atom of the following structure:

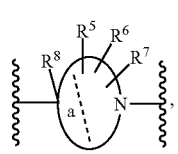

R-I with the proviso that R—I is not a para-substituted 6-membered ring;

a is —CH₂—, —CH₂CH₂—, —CH₂CH₂CH₂—, —CH₂OCH₂— or absent, wherein the —CH₂— is optionally substituted with 1-2 of —F, and wherein the —CH₂CH₂—, —CH₂CH₂CH₂—, or —CH₂OCH₂— is optionally substituted with 1-3 of —F; and wherein a forms a bridge between two non-adjacent carbons;

R⁵ is —H, —F (with the proviso that —F is not attached to a carbon also bonded to nitrogen), —CH₃, —CF₃, —CHF₂, —CH₂F, or —CH₂OH, or R⁵ represents di-substitution on a single carbon with two of —F (with the proviso that the two —F are not attached to a carbon also bonded to nitrogen) or two of —CH₃;

R⁶ and R⁷ are individually either —H, —C₁₋₃ alkyl optionally substituted with 1-3 of —F, or together they form C₁₋₃ cycloalkyl optionally substituted with 1-3 of —F;

R⁸ is —H, —F, —CH₃, —CF₃, —CHF₂, —CH₂F, or —CH₂OH, or phenyl optionally substituted with 1-3 of —F, or C₁₋₃ alkyl;

n1 and n2 can be individually either 0 or 1;

Z¹ is:

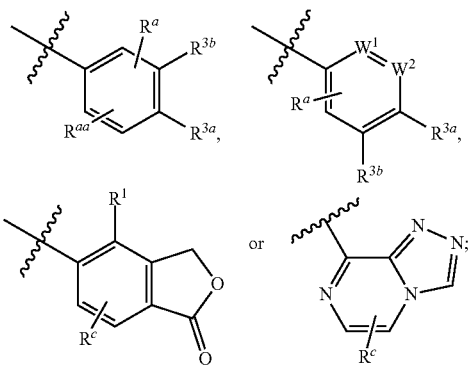

Z² is:

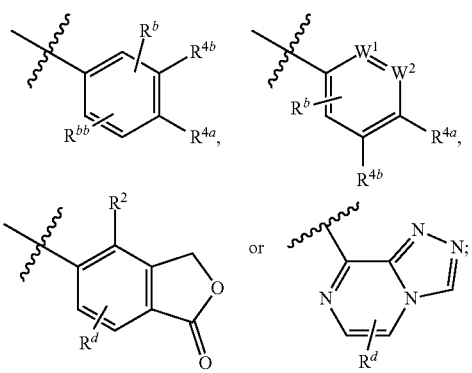

one of W¹ and W² is N and the other is CH;

R¹ and R² are each independently —H, —F, —Cl, —Br, cyclopropyl, —C₁₋₃alkyl optionally substituted with 1-3 of —F, or —OC₁₋₃alkyl optionally substituted with 1-3 of —F;

one of R³ᵃ and R³ᵇ is —CN, tetrazolyl, or S(O)₂C₍₁₋₃₎alkyl and the other is —H, —F, —Cl, —Br, —S—CH₃, —NH—CH₃, —O-cyclopropyl, —C₁₋₃alkyl optionally substituted with 1-3 of —F, or —OC₁₋₃ alkyl optionally substituted with 1-3 of —F;

one of R⁴ᵃ and R⁴ᵇ is —CN, tetrazolyl, or S(O)₂C₍₁₋₃₎alkyl and the other is —H, —F, —Cl, —Br, —S—CH₃, —NH—CH₃, —O-cyclopropyl, —C₁₋₃alkyl optionally substituted with 1-3 of —F, or —OC₁₋₃ alkyl optionally substituted with 1-3 of —F;

Rᵃ, Rᵃᵃ, Rᵇ and Rᵇᵇ are each independently —H, —F, —Cl, —C₁₋₃alkyl optionally substituted with 1 to 3 of —F, or —OC₁₋₃alkyl optionally substituted with 1 to 3 of —F;

Rᶜ and Rᵈ are each independently —H, —F, —Cl, —C₁₋₃ alkyl optionally substituted with 1 to 3 of —F, and —OC₁₋₃ alkyl optionally substituted with 1 to 3 of —F;

X is absent or C₁ alkyl having 2 substituents independently —H, or —C₁₋₃ alkyl optionally substituted with 1 to 3 of —F, wherein two —C₁₋₃ alkyl substituents together may form a C₃₋₆cycloalkyl on the C₁ alkyl; and one of Y¹ or Y² is CH(OH)—; and the other is CH(OH)—; S(O)₂—; S(O)₂CH₂—; —CH₂— (wherein —CH₂— is optionally substituted with —C₁₋₃alkyl optionally substituted with OH, —OC₁₋₃ alkyl, or –1-3 of —F), or absent; provided that where Y¹ or Y² is —S(O)₂— or S(O)₂CH₂—, then the adjacent n1 or n2, respectively, is 0; and provided further that where Y¹ or Y² is CH(OH)—, then the adjacent n1 or n2, respectively, is 1.

In Embodiment A are compounds of Formula I and pharmaceutically acceptable salts thereof wherein:

Z¹ is

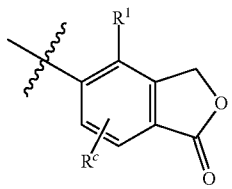

and/or Z² is

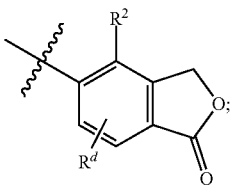

wherein the other variables are as defined herein for Formula I. In a particular subclass thereof, R¹ and/or R², if applicable, is CH₃; and Rᶜ and/or Rᵈ, if applicable, is —H. In another subclass of Embodiment A, the Y¹ or Y² adjacent the foregoing isobenzofuran Z¹ and/or Z² is —CH(OH)— and the adjacent n1 or n2 is 1.

In Embodiment B are compounds of Formula I and Embodiment A and pharmaceutically acceptable salts thereof wherein:

Z¹ is

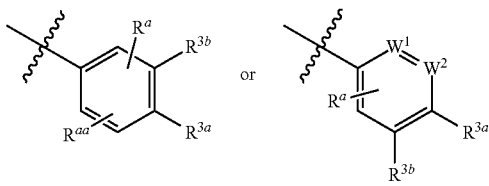

and/or
Z² is

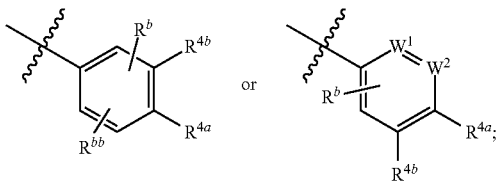

wherein the other variables are as defined herein for Formula I. In a particular subclass of Embodiment B, one of R³ᵃ and R³ᵇ, if applicable, is CN or tetrazolyl and the other is —H, —F, —Cl, —Br, —C₁₋₃alkyl optionally substituted with 1-3 of —F, or —OC₁₋₃alkyl optionally substituted with 1-3 of —F; and/or one of R⁴ᵃ and R⁴ᵇ, if applicable, is CN or tetrazolyl and the other is —H, —F, —Cl, —Br, —C₁₋₃alkyl optionally substituted with 1-3 of —F, or —OC₁₋₃alkyl optionally substituted with 1-3 of —F.

In Embodiment C are compounds of Formula I and Embodiments A and B and pharmaceutically acceptable salts thereof wherein a is —CH₂— or absent. In a particular subclass of Embodiment C, a is absent.

In Embodiment D are compounds of Formula I and Embodiments A-C and pharmaceutically acceptable salts thereof wherein R is:

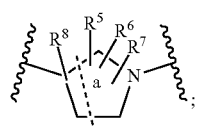

R-II wherein the other variables are as defined herein for Formula I. In a particular subclass of Embodiment D, a is absent.

In Embodiment E are compounds of Formula I and Embodiments A-D and pharmaceutically acceptable salts thereof wherein R is:

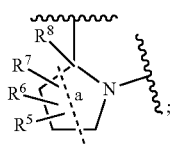

R-III wherein the other variables are as defined herein for Formula I. In a particular subclass of Embodiment E, a is absent.

In Embodiment F are compounds of Formula I and Embodiments A-D and pharmaceutically acceptable salts thereof wherein R is:

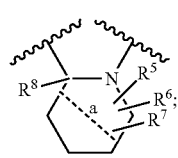

R-IV wherein the other variables are as defined herein for Formula I. In a particular subclass of Embodiment F, a is absent.

In Embodiment G are compounds of Formula I and Embodiments A-D and pharmaceutically acceptable salts thereof wherein R is:

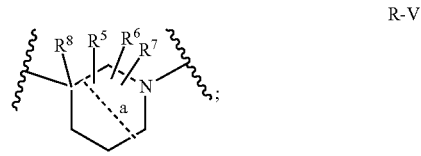

R-V wherein the other variables are as defined herein for Formula I. In a particular subclass of Embodiment G, a is absent.

In Embodiment H are compounds of Formula I and Embodiments A-D and pharmaceutically acceptable salts thereof wherein R is:

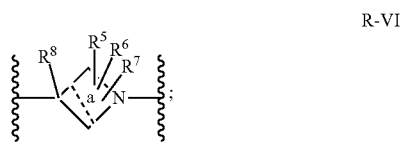

R-VI wherein the other variables are as defined herein for Formula I. In a particular subclass of Embodiment H, a is absent.

The following select embodiments of Formula I are exemplified herein. These compounds and their pharmaceutically acceptable salts form individual embodiments of the present invention:

5-{(1R)-1-Hydroxy-2-[(3R)-3-{[(2R)-2-hydroxy-2-(4-methyl-1-oxo-1,3-dihydro-2-benzofuran-5-yl)ethyl]amino}pyrrolidin-1-yl]ethyl}-4-methyl-2-benzofuran-1(3H)-one [EXAMPLE 1];

5-{(1R)-1-Hydroxy-2-[3-(1-{[(2R)-2-hydroxy-2-(4-methyl-1-oxo-1,3-dihydro-2-benzofuran-5-yl)ethyl]amino}cyclobutyl)pyrrolidin-1-yl]ethyl}-4-methyl-2-benzofuran-1(3H)-one [EXAMPLE 2];

5-{(1R)-1-Hydroxy-2-[2-({[(2R)-2-hydroxy-2-(4-methyl-1-oxo-1,3-dihydro-2-benzofuran-5-yl)ethyl]amino}methyl)pyrrolidin-1-yl]ethyl}-4-methyl-2-benzofuran-1(3H)-one [EXAMPLE 3];

5-{(1R)-1-Hydroxy-2-[2-({[2-hydroxy-1-(4-methyl-1-oxo-1,3-dihydro-2-benzofuran-5-yl)ethyl]amino}methyl)pyrrolidin-1-yl]ethyl}-4-methyl-2-benzofuran-1(3H)-one [EXAMPLE 4];

5-{(1R)-1-Hydroxy-2-[2-({[(2R)-2-hydroxy-2-(4-methyl-1-oxo-1,3-dihydro-2-benzofuran-5-yl)ethyl]amino}methyl)piperidin-1-yl]ethyl}-4-methyl-2-benzofuran-1(3H)-one [EXAMPLE 5];

5-{(1R)-1-Hydroxy-2-[2-({[2-hydroxy-1-(4-methyl-1-oxo-1,3-dihydro-2-benzofuran-5-yl)ethyl]amino}methyl)piperidin-1-yl]ethyl}-4-methyl-2-benzofuran-1(3H)-one [EXAMPLE 6];

5-{(1R)-1-Hydroxy-2-[3-({[(2R)-2-hydroxy-2-(4-methyl-1-oxo-1,3-dihydro-2-benzofuran-5-yl)ethyl]amino}methyl)-3-methylpyrrolidin-1-yl]ethyl}-4-methyl-2-benzofuran-1(3H)-one [EXAMPLE 7];

5-{(1R)-1-Hydroxy-2-[3-({[(2R)-2-hydroxy-2-(4-methyl-1-oxo-1,3-dihydro-2-benzofuran-5-yl)ethyl]amino}methyl)-3-methylpiperidin-1-yl]ethyl}-4-methyl-2-benzofuran-1(3H)-one [EXAMPLE 8];

6-{1-Hydroxy-2-[({1-[(2R)-2-hydroxy-2-(4-methyl-1-oxo-1,3-dihydro-2-benzofuran-5-yl)ethyl]pyrrolidin-2-yl}methyl)amino]ethyl}pyridine-3-carbonitrile [EXAMPLE 9];

6-(1-Hydroxy-2-((R)-1-((R)-2-hydroxy-2-(4-methyl-1-oxo-1,3-dihydroisobenzofuran-5-yl)ethyl)pyrrolidin-3-ylamino)ethyl)nicotinonitrile [EXAMPLE 10];

6-(1-Hydroxy-2-((S)-1-((R)-2-hydroxy-2-(4-methyl-1-oxo-1,3-dihydroisobenzofuran-5-yl)ethyl)pyrrolidin-3-ylamino)ethyl)nicotinonitrile [EXAMPLE 11];

6-(1-Hydroxy-2-((R)-3-((R)-2-hydroxy-2-(4-methyl-1-oxo-1,3-dihydroisobenzofuran-5-yl)ethylamino)pyrrolidin-1-yl)ethyl)nicotinonitrile [EXAMPLE 12];

6-{1-Hydroxy-2-[({1-[(2R)-2-hydroxy-2-(4-methyl-1-oxo-1,3-dihydro-2-benzofuran-5-yl)ethyl]piperidin-2-yl}methyl)amino]ethyl}pyridine-3-carbonitrile [EXAMPLE 13];

(R)-4-Cyano-N-((1-(2-hydroxy-2-(4-methyl-1-oxo-1,3-dihydroisobenzofuran-5-yl)ethyl)azetidin-3-yl)methyl)benzenesulfonamide [EXAMPLE 14];

4-Cyano-N—((R)-1-((R)-2-hydroxy-2-(4-methyl-1-oxo-1,3-dihydroisobenzofuran-5-yl)ethyl)pyrrolidin-3-yl)benzenesulfonamide [EXAMPLE 15];

(R)-1-(4-Cyanophenyl)-N-((1-(2-hydroxy-2-(4-methyl-1-oxo-1,3-dihydroisobenzofuran-5-yl)ethyl)azetidin-3-yl)methyl)methanesulfonamide [EXAMPLE 16];

5-{(1R)-1-Hydroxy-2-[(1S,4S)-6-{[(2R)-2-hydroxy-2-(4-methyl-1-oxo-1,3-dihydro-2-benzofuran-5-yl)ethyl]amino}-2-azabicyclo[2.2.1]hept-2-yl]ethyl}-4-methyl-2-benzofuran-1(3H)-one [EXAMPLE 17];

6-((1-(R)-2-Hydroxy-2-(4-methyl-1-oxo-1,3-dihydroisobenzofuran-5-yl)ethyl)pyrrolidin-2-yl)methylamino)nicotinonitrile [EXAMPLE 18];

N-((1-((R)-2-Hydroxy-2-(4-methyl-1-oxo-1,3-dihydroisobenzofuran-5-yl)ethyl)pyrrolidin-2-yl)methyl)-4-(1H-tetrazol-1-yl)benzenesulfonamide [EXAMPLE 19];

6-(3-((R)-2-Hydroxy-2-(4-methyl-1-oxo-1,3-dihydroisobenzofuran-5-yl)ethylamino)piperidin-1-yl)nicotinonitrile [EXAMPLE 20];

6-((1-((R)-2-Hydroxy-2-(4-methyl-1-oxo-1,3-dihydroisobenzofuran-5-yl)ethyl)-3-methylpyrrolidin-3-yl)methylamino)nicotinonitrile [EXAMPLE 21];

6-((1-((R)-2-Hydroxy-2-(4-methyl-1-oxo-1,3-dihydroisobenzofuran-5-yl)ethyl)-3-phenylpyrrolidin-3-yl)methylamino)nicotinonitrile [EXAMPLE 22];

5-((1R)-2-(3-(1-([1,2,4]Triazolo[4,3-c]pyrazin-8-ylamino)cyclobutyl)pyrrolidin-1-yl)-1-hydroxyethyl)-4-methylisobenzofuran-1(3H)-one [EXAMPLE 23] and 5-((1R)-2-(3-(([1,2,4]Triazolo[4,3-c]pyrazin-8-ylamino)methyl)-3-phenylpyrrolidin-1-yl)-1-hydroxyethyl)-4-methylisobenzofuran-1(3H)-one [EXAMPLE 24].

All structural Formulas and embodiments described herein include the pharmaceutically acceptable salts thereof.

As used herein except if noted otherwise, "alkyl" is intended to include both branched- and straight-chain saturated aliphatic hydrocarbon groups having the specified number of carbon atoms. Commonly used abbreviations for alkyl groups are used throughout the specification. For example the term "$C_{1-6}$ alkyl" (or "$C_1$-$C_6$ alkyl"), means linear or branched chain alkyl groups, including all isomers, having the specified number of carbon atoms and includes all of the hexyl and pentyl isomers as well as n-, iso-, sec- and tert-butyl (butyl, s-butyl, i-butyl, t-butyl; Bu=butyl), n- and i-propyl (Pr=propyl), ethyl (Et) and methyl (Me).

"Cycloalkyl" is a cyclized alkyl ring having the indicated number of carbon atoms. Examples of cycloalkyl include cyclopropyl, cyclobutyl, cyclopentyl and cyclohexyl. The cycloalkyl ring may be substituted on any available carbon which results in the creation of a stable structure, including the ring carbon which serves as the point of attachment to the rest of the molecule.

Halo or halogen refers to —F (fluoro), —Cl (chloro), —Br (bromo) and —I (iodo). Preferred halogens are —F and —Cl.

Unless expressly depicted or described otherwise, variables depicted in a structural formula with a "floating" bond, such as each of substituents $R^5$, $R^6$, $R^7$, $R^a$, $R^{aa}$, $R^b$, $R^{bb}$, $R^c$ and $R^d$ in structural Formula I, are permitted on any available carbon atom in the ring to which each is attached.

Optional substitution on a chemical moiety encompasses the presence or absence of substituents on the specified moiety. For example, —$C_{1-3}$ alkyl optionally substituted with 1-3 of —F describes unsubstituted —$C_{1-3}$ alkyl (e.g., —$CH_3$, —$CH_2CH_3$, —$(CH_2)_2CH_3$, or $CH(CH_3)_2$, or fluoro-substituted —$C_{1-3}$ alkyl including but not limited to —$CH_2F$, —$CHF_2$, —$CF_3$, or —$CH_2CF_3$.

The present invention encompasses all stereoisomeric forms of the compounds of Formula I. Centers of asymmetry that are present in the compounds of Formula I can all independently of one another have (R) configuration or (S) configuration. When bonds to the chiral carbon are depicted as straight lines in the structural Formulas of the invention, it is understood that both the (R) and (S) configurations of the chiral carbon, or when a compound name is recited without a chiral designation for a chiral carbon, it is understood that both the (R) and (S) configurations of the chiral carbon, and hence both enantiomers and mixtures thereof, are embraced within the Formula or by the name. The production of specific stereoisomers or mixtures thereof may be identified in the Examples where such stereoisomers or mixtures were obtained, but this in no way limits the inclusion of all stereoisomers and mixtures thereof from being within the scope of this invention.

The invention includes all possible enantiomers and diastereomers and mixtures of two or more stereoisomers, for example mixtures of enantiomers and/or diastereomers, in all ratios. Thus, enantiomers are a subject of the invention in enantiomerically pure form, both as levorotatory and as dextrorotatory antipodes, in the form of racemates and in the form of mixtures of the two enantiomers in all ratios. In the case of a cistrans isomerism the invention includes both the cis form and the trans form as well as mixtures of these forms in all ratios. The preparation of individual stereoisomers can be carried out, if desired, by separation of a mixture by customary methods, for example by chromatography or crystallization, by the use of stereochemically uniform starting materials for the synthesis or by stereoselective synthesis. Optionally a derivatization can be carried out before a separation of stereoisomers. The separation of a mixture of stereoisomers can be carried out at an intermediate step during the synthesis of any compound of Formula I or it can be done on a final racemic product. Absolute stereochemistry may be determined by X-ray crystallography of crystalline products or crystalline intermediates which are derivatized, if necessary, with a reagent containing a stereogenic center of known configuration. Where compounds of this invention are capable of tautomerization, all individual tautomers as well as mixtures thereof are included in the scope of this invention. The present invention includes all such isomers, as well as salts, solvates (including hydrates) and solvated salts of such racemates, enantiomers, diastereomers and tautomers and mixtures thereof.

Reference to the compounds of Formula I herein encompasses the compounds of Formula I and all embodiments thereof. Reference to the compounds of this invention as those of a specific formula or embodiment, e.g., Formula I and embodiments thereof, or any other generic structural formula or specific compound described or claimed herein, is intended to encompass the specific compound or compounds falling within the scope of the formula or embodiment, including salts thereof, particularly pharmaceutically acceptable salts, solvates of such compounds and solvated salt forms thereof, where such forms are possible unless specified otherwise.

In the compounds of Formula I, the atoms may exhibit their natural isotopic abundances, or one or more of the atoms may be artificially enriched in a particular isotope having the same atomic number, but an atomic mass or mass number different from the atomic mass or mass number predominantly found in nature. The present invention is meant to include all suitable isotopic variations of the compounds of Formula I. For example, different isotopic forms of hydrogen (H) include protium ($^1$H) and deuterium ($^2$H). Protium is the predominant hydrogen isotope found in nature. Enriching for deuterium may afford certain therapeutic advantages, such as increasing in vivo half-life or reducing dosage requirements, or may provide a compound useful as a standard for characterization of biological samples. Isotopically-enriched compounds within Formula I can be prepared without undue experimentation by conventional techniques well known to those skilled in the art or by processes analogous to those described in the Schemes and Examples herein using appropriate isotopically-enriched reagents and/or intermediates.

When the compounds of Formula I contain one or more acidic or basic groups the invention also includes the corresponding pharmaceutically acceptable salts. Thus, the compounds of Formula I which contain acidic groups can be used according to the invention, for example, as alkali metal salts, alkaline earth metal salts or as ammonium salts. Examples of such salts include but are not limited to sodium salts, potassium salts, calcium salts, magnesium salts or salts with ammonia or organic amines such as, for example, ethylamine, ethanolamine, triethanolamine or amino acids. Compounds of Formula I which contain one or more basic groups, i.e. groups which can be protonated, can be used according to the invention in the form of their acid addition salts with inorganic or organic acids as, for example but not limited to, salts with hydrogen chloride, hydrogen bromide, phosphoric acid, sulfuric acid, nitric acid, benzenesulfonic acid, methanesulfonic acid, p-toluenesulfonic acid, naphthalenedisulfonic acids, oxalic acid, acetic acid, trifluoroacetic acid, tartaric acid, lactic acid, salicylic acid, benzoic acid, formic acid, propionic acid, pivalic acid, diethylacetic acid, malonic acid, succinic acid, pimelic acid, fumaric acid, maleic acid, malic acid, sulfaminic acid, phenylpropionic acid, gluconic acid, ascorbic acid, isonicotinic acid, citric acid, adipic acid, etc. If the compounds of Formula I simultaneously contain acidic and basic groups in the molecule the invention also includes, in addition to the salt forms mentioned, inner salts or betaines (zwitterions). Salts can be obtained from the compounds of Formula I by customary methods which are known to the person skilled in the art, for example by combination with an organic or inorganic acid or base in a solvent or dispersant, or by anion exchange or cation exchange from other salts. The present invention also includes all salts of the compounds of Formula I which, owing to low physiological compatibility, are not directly suitable for use in pharmaceuticals but which can be used, for example, as intermediates for chemical reactions or for the preparation of physiologically (i.e., pharmaceutically) acceptable salts.

Furthermore, compounds of the present invention may exist in amorphous form and/or one or more crystalline forms, and as such all amorphous and crystalline forms and mixtures thereof of the compounds of Formula I are intended to be included within the scope of the present invention. In addition, some of the compounds of the instant invention may form solvates with water (i.e., a hydrate) or common organic solvents. Such solvates and hydrates, particularly the pharmaceutically acceptable solvates and hydrates, of the instant compounds are likewise encompassed within the scope of this invention, along with un-solvated and anhydrous forms.

Any pharmaceutically acceptable pro-drug modification of a compound of this invention which results in conversion in vivo to a compound within the scope of this invention is also within the scope of this invention. For example, esters can optionally be made by esterification of an available carboxylic acid group or by formation of an ester on an available hydroxy group in a compound. Similarly, labile amides can be made. Pharmaceutically acceptable esters or amides of the compounds of this invention may be prepared to act as pro-drugs which can be hydrolyzed back to an acid (or —COO— depending on the pH of the fluid or tissue where conversion takes place) or hydroxy form particularly in vivo and as such are encompassed within the scope of this invention. Examples of pharmaceutically acceptable pro-drug modifications include, but are not limited to, —$C_{1-6}$ alkyl esters and —$C_{1-6}$ alkyl substituted with phenyl esters.

Accordingly, the compounds within the generic structural formulas, embodiments and specific compounds described and claimed herein encompass salts, all possible stereoisomers and tautomers, physical forms (e.g., amorphous and crystalline forms), solvate and hydrate forms thereof and any combination of these forms, as well as the salts thereof, pro-drug forms thereof, and salts of pro-drug forms thereof, where such forms are possible unless specified otherwise.

The compounds of Formula I according to the invention are inhibitors of ROMK, and are therefore useful as diuretic and/or natriuretic agents. ROMK inhibitors help to increase urination and increase urine volume and also to prevent or reduce reabsorption of sodium in the kidneys leading to increased excretion of sodium and water. Therefore, the compounds are useful for treatment or prophylaxis of disorders that benefit from increased excretion of water and sodium from the body. Accordingly, the present invention provides a method for inhibiting ROMK comprising administering a compound of Formula I in a ROMK-inhibitory effective amount to a patient in need thereof. The inhibition of ROMK by the compounds of Formula I can be examined, for example, in any of the activity assays described below. The invention also provides a method for causing diuresis, natriuresis or both, comprising administering a compound of Formula I in a therapeutically effective amount to a patient in need thereof.

Due to their activity as diuretics and natriuretic agents, this invention further provides the use of compounds of Formula I in methods for treatment of, prevention of or reduction of risk for developing medical conditions that benefit from increased excretion of water and sodium, such as but not limited to one or more of hypertension, heart failure (both acute and chronic, the latter also known as congestive heart failure) and/or other conditions resulting from excessive salt and water retention. It further includes the use of the compounds of Formula I in methods for treatment of, prevention of or reduction of risk for developing one or more disorders such as pulmonary arterial hypertension (PAH), cardiovascular disease, diabetes mellitus, diabetes insipidus, post-operative volume overload, endothelial dysfunction, diastolic dysfunction, systolic dysfunction, stable and unstable angina pectoris, thromboses, restenosis, myocardial infarction, stroke, cardiac insufficiency, pulmonary hypertonia, atherosclerosis, hepatic cirrhosis, ascites, pre-eclampsia, cerebral edema, nephropathy, glomerulonephritis, nephrotic syndrome, acute and chronic kidney insufficiency, acute tubular necrosis, hypercalcemia, idiopathic edema, Dent's disease, Meniere's disease, edetamous states, glaucoma, benign intracranial hypertension, and other conditions for which a diuretic would have therapeutic or prophylactic benefit. The compounds of the invention can be administered to a patient having, or at risk of having, one or more conditions for which a diuretic would have therapeutic or prophylactic benefit such as those described herein.

In general, compounds that are ROMK inhibitors can be identified as those compounds which, when tested, have an $IC_{50}$ of 5 µM or less, preferably 1 µM or less, and more preferably 0.25 µM or less, in at least one of the following assays: 1) the Electrophysiology Assay and 2) the Thallium Flux Assay. These assays are described in more detail further below.

The dosage amount of the compound to be administered depends on the individual case and is, as is customary, to be adapted to the individual circumstances to achieve an optimum effect. Thus, it depends on the nature and the severity of the disorder to be treated, and also on the sex, age, weight and individual responsiveness of the human or animal to be treated, on the efficacy and duration of action of the compounds used, on whether the therapy is acute or chronic or prophylactic, or on whether other active compounds are administered in addition to the compounds of Formula I. A consideration of these factors is well within the purview of the ordinarily skilled clinician for the purpose of determining the therapeutically effective or prophylactically effective dosage amount needed to prevent, counter, or arrest the progress of the condition. It is expected that the compound will be administered chronically on a daily basis for a length of time appropriate to treat or prevent the medical condition relevant to the patient, including a course of therapy lasting days, months, years or the life of the patient.

In general, a daily dose of approximately 0.001 to 100 mg/kg, preferably 0.001 to 30 mg/kg, in particular 0.001 to 10 mg/kg (in each case mg per kg of bodyweight) is appropriate for administration to an adult weighing approximately 75 kg in order to obtain the desired results. The daily dose is preferably administered in a single dose or can be divided into several, for example two, three or four individual doses, and may be, for example but not limited to, 0.1 mg, 0.25 mg, 0.5 mg, 0.75 mg, 1 mg, 1.25 mg, 2 mg, 2.5 mg, 5 mg, 10 mg, 20 mg, 40 mg, 50 mg, 75 mg, 100 mg, 125 mg, 150 mg, 175 mg, 200 mg, etc., on a daily basis. In some cases, depending on the individual response, it may be necessary to deviate upwards or downwards from the given daily dose. Furthermore, the compound may be formulated for immediate or modified release such as extended or controlled release.

The term "patient" includes animals, preferably mammals and especially humans, who use the instant active agents for the prophylaxis or treatment of a medical condition. Administering of the drug to the patient includes both self-administration and administration to the patient by another person. The patient may be in need of treatment for an existing disease or medical condition, or may desire prophylactic treatment to prevent or reduce the risk for developing said disease or medical condition or developing long-term complications from a disease or medical condition.

The term therapeutically effective amount is intended to mean that amount of a drug or pharmaceutical agent that will elicit the biological or medical response of a tissue, a system, animal or human that is being sought by a researcher, veterinarian, medical doctor or other clinician. A prophylactically effective amount is intended to mean that amount of a pharmaceutical drug that will prevent or reduce the risk of occurrence of the biological or medical event that is sought to be prevented in a tissue, a system, animal or human by a researcher, veterinarian, medical doctor or other clinician. It is understood that a specific daily dosage amount can simultaneously be both a therapeutically effective amount, e.g., for treatment of hypertension, and a prophylactically effective amount, e.g., for prevention or reduction of risk of myocardial infarction or prevention and reduction of risk for complications related to hypertension.

In the methods of treatment of this invention, the ROMK inhibitors may be administered via any suitable route of administration such as, for example, orally, parenterally, or rectally in dosage unit formulations containing conventional non-toxic pharmaceutically acceptable carriers, adjuvants and vehicles. The term parenteral as used herein includes subcutaneous injections, intravenous, intramuscular, intrasternal injection or infusion techniques. Oral formulations are preferred for treatment of chronic indications such as hypertension or chronic heart failure, particularly solid oral dosage units such as pills, tablets or capsules, and more particularly tablets. IV dosing is preferred for acute treatment, for example, for the treatment of acute heart failure.

This invention also provides pharmaceutical compositions comprised of a compound of Formula I and a pharmaceutically acceptable carrier which is comprised of one or more excipients or additives. An excipient or additive is an inert substance used to formulate the active drug ingredient. For oral use, the pharmaceutical compositions of this invention containing the active ingredient may be in forms such as pills, tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions. Tablets contain the active ingredient in admixture with non-toxic pharmaceutically acceptable excipients, which are suitable for the manufacture of tablets. These excipients may be for example, inert diluents, such as calcium carbonate, sodium carbonate, lactose, mannitol, calcium phosphate or sodium phosphate; granulating and disintegrating agents, for example, corn starch, or alginic acid; binding agents, for example starch, gelatin or acacia, and lubricating agents, for example, magnesium stearate, stearic acid or talc.

Pharmaceutical compositions may also contain other customary additives, for example, wetting agents, stabilizers, emulsifiers, dispersants, preservatives, sweeteners, colorants, flavorings, aromatizers, thickeners, buffer substances, solvents, solubilizers, agents for achieving a depot effect, salts for altering the osmotic pressure, coating agents or antioxidants.

Oral immediate-release and time-controlled release dosage forms may be employed, as well as enterically coated oral dosage forms. Tablets may be uncoated or they may be coated by known techniques for aesthetic purposes, to mask taste or for other reasons. Coatings can also be used to delay disintegration and absorption in the gastrointestinal tract and thereby provide a sustained action over a longer period. For example, a time delay material such as glyceryl monostearate or glyceryl distearate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredients is mixed with water or miscible solvents such as propylene glycol, PEGs and ethanol, or an oil medium, for example peanut oil, liquid paraffin, or olive oil.

Aqueous suspensions contain the active material in admixture with excipients suitable for the manufacture of aqueous suspensions. Oily suspensions may be formulated by suspending the active ingredient in a vegetable oil, for example arachis oil, olive oil, sesame oil or coconut oil, or in mineral oil such as liquid paraffin. The oily suspensions may contain a thickening agent, for example beeswax, hard paraffin or cetyl alcohol. Sweetening agents and flavoring agents may be added to provide a palatable oral preparation. These compositions may be preserved by the addition of an anti-oxidant such as ascorbic acid. Syrups and elixirs may be formulated with sweetening agents, for example glycerol, propylene glycol, sorbitol or sucrose.

The instant invention also encompasses a process for preparing a pharmaceutical composition comprising combining a compound of Formula I with a pharmaceutically acceptable carrier. Also encompassed is the pharmaceutical composition which is made by combining a compound of Formula I with a pharmaceutically acceptable carrier. Furthermore, a therapeutically effective amount of a compound of this invention can be used for the preparation of a medicament useful for inhibiting ROMK, for causing diuresis and/or natriuresis, and/or for treating, preventing or reducing the risk for any of the medical conditions described herein, in dosage amounts described herein.

The amount of active compound of Formula I and/or its pharmaceutically acceptable salts in the pharmaceutical composition may be, for example but not limited to, from 0.1 to 200 mg, particularly from 0.1 to 100 mg, and more particularly from 0.1 to 50 mg, per dose on a free acid/free base weight basis, but depending on the type of the pharmaceutical composition, potency of the active ingredient and/or the medical condition being treated, it could also be lower or higher. Pharmaceutical compositions usually comprise 0.5 to 90 percent by weight of the active compound on a free acid/free base weight basis.

The compounds of Formula I inhibit ROMK. On account of this property, apart from use as pharmaceutically active compounds in human medicine and veterinary medicine, they can also be employed as a scientific tool or as aid for biochemical investigations in which such an effect on ROMK is intended, and also for diagnostic purposes, for example in the in vitro diagnosis of cell samples or tissue samples. The compounds of Formula I can also be employed as intermediates for the preparation of other pharmaceutically active compounds.

One or more additional pharmacologically active agents may be administered in combination with a compound of Formula I. An additional active agent (or agents) is intended to mean a compound that is different from the compound of Formula I, and which is a pharmaceutically active agent (or agents) that is active in the body, including pro-drugs that convert to pharmaceutically active form after administration, and also includes free-acid, free-base, and pharmaceutically acceptable salts of said additional active agents when such forms are sold commercially or are otherwise chemically possible. Generally, any suitable additional active agent or agents, including but not limited to anti-hypertensive agents, additional diuretics, anti-atherosclerotic agents such as a lipid modifying compound, anti-diabetic agents and/or anti-obesity agents may be used in any combination with the compound of Formula I in a single dosage formulation (a fixed dose drug combination), or may be administered to the patient in one or more separate dosage formulations which allows for concurrent or sequential administration of the active agents (co-administration of the separate active agents). Examples of additional active agents which may be employed include but are not limited to angiotensin converting enzyme inhibitors (e.g, alacepril, benazepril, captopril, ceronapril, cilazapril, delapril, enalapril, enalaprilat, fosinopril, imidapril, lisinopril, moveltipril, perindopril, quinapril, ramipril, spirapril, temocapril, or trandolapril), angiotensin II receptor antagonists also known as angiotensin receptor blockers or ARBs (e.g., losartan i.e., COZAAR®, valsartan, candesartan, olmesartan, telmesartan, eprosartan, irbesartan, azilsartan and any of these drugs used in combination with thiazide-like diuretics such as hydrochlorothiazide such as HYZAAR®), diuretics, e.g., hydrochlorothiazide (HCTZ); potassium sparing diuretics such as amiloride HCl, spironolactone, eplerenone, triamterene, each with or without HCTZ; carbonic anhydrase inhibitors, such as acetazolamide, neutral endopeptidase inhibitors (e.g., thiorphan and phosphoramidon), aldosterone antagonists, aldosterone synthase inhibitors, renin inhibitors (e.g. urea derivatives of di- and tri-peptides (See U.S. Pat. No. 5,116,835), amino acids and derivatives (U.S. Pat. Nos. 5,095,119 and 5,104,869), amino acid chains linked by non-peptidic bonds (U.S. Pat. No. 5,114,937), di- and tri-peptide derivatives (U.S. Pat. No. 5,106,835), peptidyl amino diols (U.S. Pat. Nos. 5,063,208 and 4,845,079) and peptidyl beta-aminoacyl aminodiol carbamates (U.S. Pat. No. 5,089,471); also, a variety of other peptide analogs as disclosed in the following U.S. Pat. Nos. 5,071,837; 5,064,965; 5,063,207; 5,036,054; 5,036,053; 5,034,512 and 4,894,437, and small molecule renin inhibitors (including diol sulfonamides and sulfinyls (U.S. Pat. No. 5,098,924), N-morpholino derivatives (U.S. Pat. No. 5,055,466), N-heterocyclic alcohols (U.S. Pat. No. 4,885,292) and pyrolimidazolones (U.S. Pat. No. 5,075,451); also, pepstatin derivatives (U.S. Pat. No. 4,980,283) and fluoro- and chloro-derivatives of statone-containing peptides (U.S. Pat. No. 5,066,643), enalkrein, RO 42-5892, A 65317, CP 80794, ES 1005, ES 8891, SQ 34017, aliskiren (2(S),4(S),5(S),7(S)—N-(2-carbamoyl-2-methylpropyl)-5-amino-4-hydroxy-2,7-diisopropyl-8-[4-methoxy-3-(3-methoxypropoxy)-phenyl]-octanamid hemifumarate) SPP600, SPP630 and SPP635), endothelin receptor antagonists, mineralocorticoid receptor antagonists, vasodilators (e.g. nitroprusside), calcium channel blockers (e.g., amlodipine, nifedipine, veraparmil, diltiazem, felodipine, gallopamil, niludipine, nimodipine, nicardipine), potassium channel activators (e.g., nicorandil, pinacidil, cromakalim, minoxidil, aprilkalim, loprazolam), sympatholitics, beta-adrenergic blocking drugs (e.g., acebutolol, atenolol, betaxolol, bisoprolol, carvedilol, metoprolol, metoprolol tartate, nadolol, propranolol, sotalol, timolol), alpha adrenergic blocking drugs (e.g., doxazocin, prazocin or alpha methyldopa); central alpha adrenergic agonists; peripheral vasodilators (e.g. hydralazine); nitrates or nitric oxide donating compounds, e.g., isosorbide mononitrate, lipid lowering agents (e.g., HMG-CoA reductase inhibitors such as simvastatin and lovastatin which are marketed as ZOCOR® and MEVACOR® in lactone pro-drug form and function as inhibitors after administration, and pharmaceutically acceptable salts of dihydroxy open ring acid HMG-CoA reductase inhibitors such as atorvastatin (particularly the calcium salt sold in LIPITOR®, rosuvastatin (particularly the calcium salt sold in CRESTOR®), pravastatin (particularly the sodium salt sold in PRAVACHOL®), and fluvastatin (particularly the sodium salt sold in LESCOL®); a cholesterol absorption inhibitor such as ezetimibe (ZETIA®), and ezetimibe in combination with any other lipid lowering agents such as the HMG-CoA reductase inhibitors noted above and particularly with simvastatin (VYTORIN®) or with atorvastatin calcium;

niacin in immediate-release or controlled release forms, and particularly niacin in combination with a DP antagonist such as laropiprant (TREDAPTIVE®) and/or with an HMG-CoA reductase inhibitor; niacin receptor agonists such as acipimox and acifran, as well as niacin receptor partial agonists; metabolic altering agents including insulin sensitizing agents and related compounds for the treatment of diabetes such as biguanides (e.g., metformin), meglitinides (e.g., repaglinide, nateglinide), sulfonylureas (e.g., chlorpropamide, glimepiride, glipizide, glyburide, tolazamide, tolbutamide), thiazolidinediones also referred to as glitazones (e.g., pioglitazone, rosiglitazone), alpha glucosidase inhibitors (e.g., acarbose, miglitol), dipeptidyl peptidase inhibitors, e.g., (sitagliptin (JANUVIA®), alogliptin, vildagliptin, saxagliptin, linagliptin, dutogliptin, gemigliptin), ergot alkaloids (e.g., bromocriptine), combination medications such as JANUMET® (sitagliptin with metformin), and injectable diabetes medications such as exenatide and pramlintide acetate; or with other drugs beneficial for the prevention or the treatment of the above-mentioned diseases including but not limited to diazoxide; and including the free-acid, free-base, and pharmaceutically acceptable salt forms of the above active agents where chemically possible.

Several methods for preparing the compounds of this invention are described in the following Schemes and Examples. Starting materials and intermediates are purchased from commercial sources, made from known procedures, or are otherwise illustrated. In some cases the order of carrying out the steps of the reaction schemes may be varied to facilitate the reaction or to avoid unwanted reaction products. The Ar group shown in the below schemes can represent any of the mono-or-bi-cyclic rings at the terminal end of $Z^1$ or $Z^2$ as defined previously.

Synthesis of the compounds disclosed herein is generally provided for in the following schemes.

The preparation of the compounds I1 is detailed in Scheme 1. Treatment of the styrene epoxide 1-1 with an appropriate monoprotected diamine 1-2 under appropriate coupling conditions (such as heating in alcoholic solvent, or microwave heating) affords the amino alcohol product 1-3. The Boc protecting group (Greene, T.; Wuts, P. G. M. *protective Groups in Organic Synthesis*, John Wiley and Sons, Inc., New York, N.Y. 1991) of 1-3 can be removed under acidic conditions, such as with TFA or HCl. Alternatively, the diamine may be protected with another protecting group such as Cbz, and subsequently removed by hydrogenolysis. For optimal regioselectivity in the epoxide opening the free base of the resulting amine should be generated in situ (as described in the preparation of EXAMPLE 1, for instance) or isolated previously through standard methods (for example sodium carbonate wash and extraction, ion exchange column chromatography, etc.). The resulting amine may be coupled to another epoxide 1-5 (which may or may not be the same as 1-1) under the conditions described above to provide compounds I1.

SCHEME 1

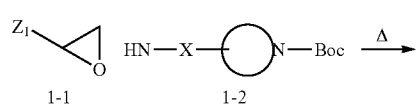

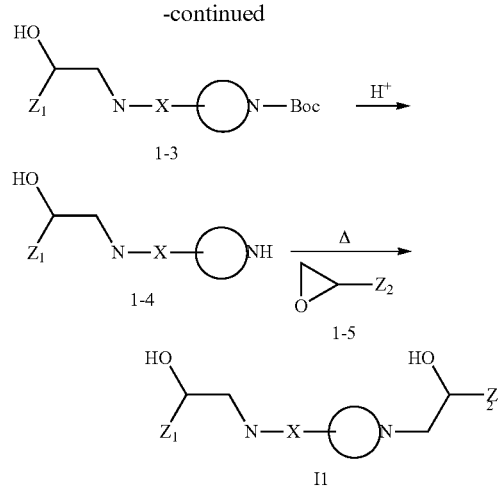

Alternately, the same operations can be carried out as depicted in Scheme 2 for compounds where the Boc protecting group is initially present on the exocyclic nitrogen (2-1).

SCHEME 2

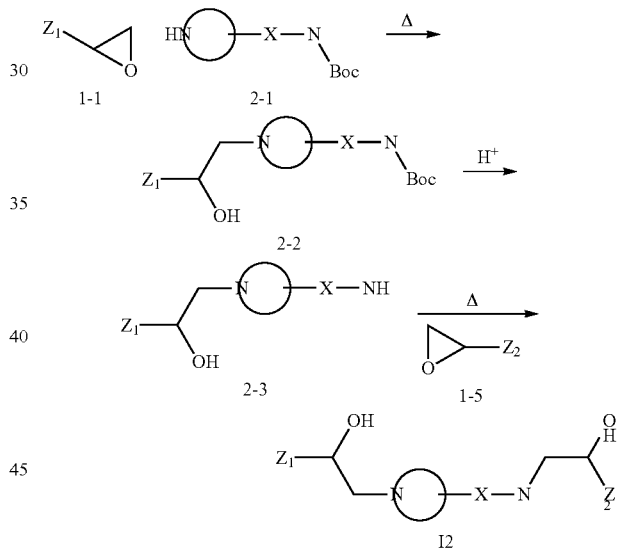

Additionally, compounds of formulas I3 and I4 can also be prepared by the sequences detailed in Schemes 2 and 3. Treatment of the previously described intermediates 1-4 or 2-3 with the appropriate electrophile 2-1 (such as carboxylic acid or ester) under standard amide bond forming conditions (such as EDC, HOBt, triethylamine) gives rise to I2 or I3.

SCHEME 3

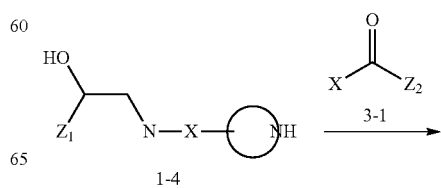

-continued

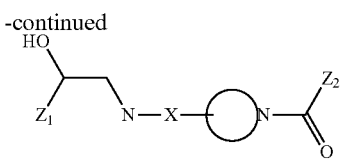
I3

SCHEME 4

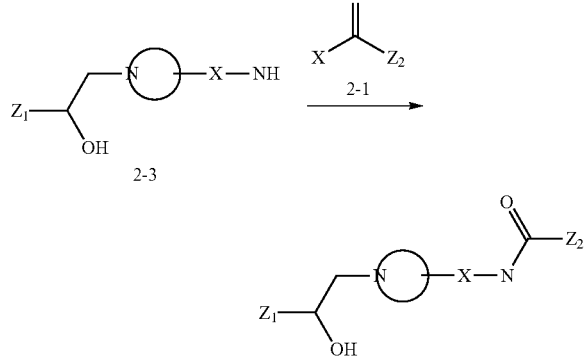

The preparation of compounds of formulas I5 and I6 is shown in Schemes 5 and 6. Again, starting from intermediates 1-4 or 2-3, coupling with the appropriate sulfonic acid or activated derivative (such as sulfonyl chloride) under appropriate conditions (such as triethylamine) provides the sulfonamides I5 or I6.

SCHEME 5

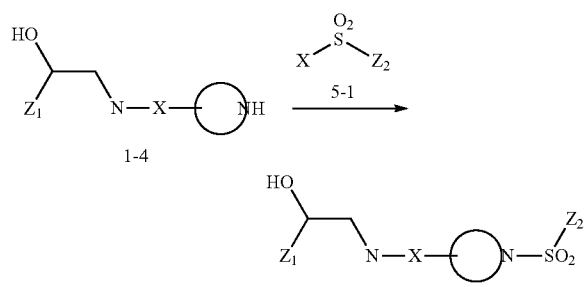

SCHEME 6

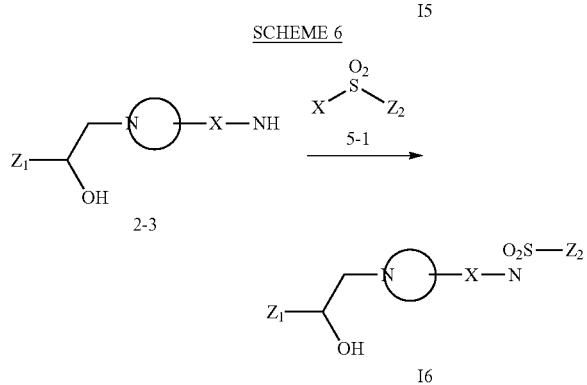

Compounds described by the formulas I7 and I8 can be prepared following the methods detailed in Schemes 7 and 8. Treatment of 1-4 (as described above in Scheme 1) or 2-3 (as described above in Scheme 2) with the appropriate aryl or heteroaryl halide, trifluoromethanesulfonate, phosphonate, or other reactive intermediate under metal catalyzed cross coupling (such as Buchwald conditions) affords I7 or I8.

SCHEME 7

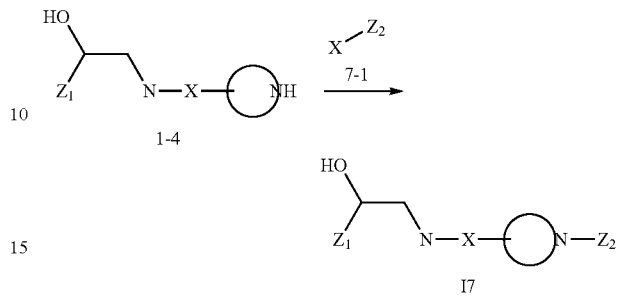

SCHEME 8

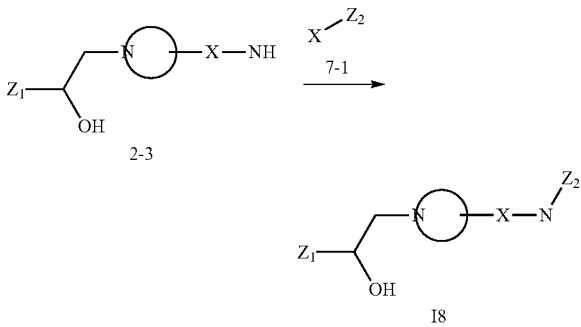

General Procedures.

The independent synthesis of diastereomers and enantiomers or their chromatographic separations may be achieved as known in the art by appropriate modification of the methodology disclosed herein. Their absolute stereochemistry may be determined by x-ray crystallography of crystalline products or crystalline intermediates which are derivatized, if necessary, with a reagent containing an asymmetric center of known absolute stereochemistry.

The subject compounds may be prepared by modification of the procedures disclosed in the Examples as appropriate. Starting materials are commercially available or made by known procedures or as illustrated. The following examples are provided for the purpose of further illustration only and are not intended to be limitations of the disclosed invention.

Reactions sensitive to moisture or air were performed under nitrogen or argon using anhydrous solvents and reagents. The progress of reactions was determined by either analytical thin layer chromatography (TLC) usually performed with E. Merck precoated TLC plates, silica gel 60F-254, layer thickness 0.25 mm or liquid chromatography-mass spectrometry (LC-MS; also referred to as "LC" in the experimental procedures herein).

Typically the analytical LC-MS system used consisted of a Waters® ZQ™ platform with electrospray ionization in positive ion detection mode with an Agilent® 1100 series HPLC with autosampler. The column was usually a Waters® Xterra® MS C18, 3.0×50 mm, 5 µm. The flow rate was 1 mL/minute, and the injection volume was 10 µL. UV detection was in the range of 210-400 nm. The mobile phase consisted of solvent A (water plus 0.06% TFA) and solvent B (acetonitrile plus 0.05% TFA) with a gradient of 100% solvent A for 0.7 minutes changing to 100% solvent B over 3.75 minutes, maintained for 1.1 minutes, then reverting to 100% solvent A over 0.2 minutes.

Preparative High Performance Liquid Chromatography (HPLC) purifications were usually performed using a mass spectrometry directed system. Usually they were performed on a Waters® Chromatography Workstation configured with LC-MS System Consisting of: Waters® ZQ™ single quad MS system with Electrospray Ionization, Waters® 2525 Gradient Pump, Waters® 2767 Injector Collector, Waters® 996 PDA Detector, the MS Conditions of: 150-750 amu, Positive Electrospray, Collection Triggered by MS, and a Waters® Sunfire C-18 5 micron, 30 min (id)×100 mm column. The mobile phases consisted of mixtures of acetonitrile (10-100%) in water containing 0.1% TFA. Flow rates were maintained at 50 mL/minute, the injection volume was 1800 µL, and the UV detection range was 210-400 nm. Mobile phase gradients were optimized for the individual compounds.

Reactions performed using microwave irradiation were normally carried out using an Emrys™ Optimizer manufactured by Personal Chemistry, or an Initiator manufactured by Biotage.

Concentration of solutions was carried out on a rotary evaporator under reduced pressure. Flash chromatography was usually performed using a Biotage Flash Chromatography apparatus (Dyax Corp.) on silica gel (32-63 mM, 60 Å pore size) in pre-packed cartridges of the size noted. $^1$H NMR spectra were acquired at 500 MHz spectrometers in CDCl$_3$ solutions unless otherwise noted. Chemical shifts were reported in parts per million (ppm). Tetramethylsilane (TMS) was used as internal reference in CD$_3$Cl solutions, and residual CH$_3$OH peak or TMS was used as internal reference in CD$_3$OD solutions. Coupling constants (J) were reported in hertz (Hz). Chiral analytical chromatography was performed on one of Chiralpak® AS, Chiralpak® AD, Chiralcel® OD, Chiralcel® IA, or Chiralcel® OJ columns (250×4.6 mm) (Daicel Chemical Industries, Ltd.) with noted percentage of either ethanol in hexane (% Et/Hex) or isopropanol in heptane (% IPA/Hep) as isocratic solvent systems. Chiral preparative chromatography was conducted on one of Chiralpak® AS, Chiralpak® AD, Chiralcel® OD, Ciralcel® IA, or Chiralcel® OJ columns (20×250 mm) (Daicel Chemical Industries, Ltd.) with desired isocratic solvent systems identified on chiral analytical chromatography or by supercritical fluid (SFC) conditions.

In the Examples, when a compound is obtained via chromatography (e.g., MPLC, HPLC, silica gel), it means that the solvent was removed (generally under vacuum) after the chromatography step to obtain the isolated product.

Abbreviations used herein include: —C(O)CH$_3$ (Ac); acetic acid (AcOH); —OC(O)CH$_3$ (OAc); aqueous (aq); Cbz (benzyloxycarbonyl); N;N-diisopropylethylamine (DIEA); N;N-dimethylformamide (DMF); ethyl acetate (EtOAc); diethyl ether (ether or Et$_2$O); petroleum ether (Pet Ether; PE); gram(s) (g); hour(s) (h or hr); 2-propanol (IPA); mass spectrum (ms or MS); microliter(s) (4); milligram(s) (mg); milliliter(s) (mL); millimole (mmol); minute(s) (min); methyl t-butylether (MTBE); (benzotriazol-1-yloxy)tripyrrolidinophosphonium hexafluorophosphate (PyBOP); retention time (R$_t$); room temperature (rt or RT); saturated aq sodium chloride solution (brine); trifluoroacetic acid (TFA); triethylamine (TEA); hydrochloric acid (HCl); tetrahydrofuran (THF); flash chromatography (FC); medium pressure liquid chromatography (MPLC); liquid chromatography (LC); liquid chromatography-mass spectrometry (LCMS or LC-MS); supercritical fluid chromatography (SFC); t-butyloxycarbonyl (Boc or BOC); Diethylaminosulfur trifluoride (DAST); dichloromethane (DCM); dimethylacetamide (DMA; DMAC); dimethylsulfoxide (DMSO); 1,3-Bis(diphenylphosphino)propane (DPPP); acetic acid (HOAc); 3-chloroperoxybenzoic acid (m-CPBA); methyl (Me); methanol (MeOH); N-bromosuccinamide (NBS); thin layer chromatography (TLC); N-(3-dimethylaminopropyl)-N'-ethylcarbdiimide hydrochloride (EDC); round bottom (RB); diisopropylamine (DIPA); hexamethylphosphoramide (HMPA); 1-hydroxybenzotriazole (HOBt); lithium diisopropylamide (LDA); high performance liquid chromatography/mass spectrometry (HPLC-MS); nicotinamide adenine dinucleotide (NADP); isopropyl acetate (IPAc); O-(Benzotriazol-1-yl)-N,N,N',N'-tetramethyluronium tetrafluoroborate (TBTU). Celite® is a tradename for diatomaceous earth.

The following are representative procedures for the preparation of the compounds used in the following Examples, or which can be substituted for the compounds used in the following Examples which may not be commercially available.

Intermediate 1

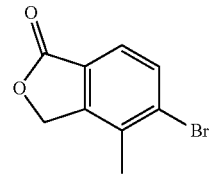

5-Bromo-4-Methyl-2-benzofuran-1(3H)-one

Step A: (3-Bromo-2-methylphenyl)methanol

To a solution of 3-bromo-2-methyl benzoic acid (35 g, 160 mmol) in THF (200 mL) was added borane THF complex (1.0 M, 210 mL, 210 mmol). The mixture was allowed to stir for 24 hours. The reaction was quenched with water. The solvent THF was removed under reduced pressure. The resulting solid was dissolved in ethyl acetate (500 mL), washed with 1N hydrochloric acid, saturated sodium bicarbonate, and brine. The combined organic layers were dried over sodium sulfate and concentrated to afford (3-bromo-2-methylphenyl)methanol.

Step B: 5-Bromo-4-methyl-2-benzofuran-1(3H)-one

To a flask charged with (3-bromo-2-methylphenyl)methanol (6.0 g, 30 mmol) was added a 1M trifluoroacetic acid solution of thallium trifluoroacetate (16.2 g, 29.8 mmol). The mixture was stirred at room temperature overnight. The solvent was removed under vacuum, and the residue was pumped under high vacuum for 30 minutes to ensure complete removal of TFA. To the residue was then added palladium(II) chloride (529 mg, 2.98 mmol), lithium chloride (2.53 g, 59.7 mmol), magnesium oxide (2.41 g, 59.7 mmol), and methanol (150 mL). The reaction was flushed with CO twice, and kept under CO at room temperature. Analysis by LC showed a big product spot within 2 hours. To this solution was added ethyl acetate to precipitate the salts. The black solution was filtered through a Celite® diatomaceous earth pad, washed with EtOAc, adsorbed onto silica and purified by silica gel chromatography to afford 5-bromo-4-methyl-2-benzofuran-1(3H)-one.

$^1$H-NMR (500 MHz, CDCl$_3$) δ ppm 7.71 (d, J=8.0 Hz, 1H), 7.58 (d, J=8.0 Hz, 1H), 5.25 (s, 2H), 2.37 (s, 3H).

Intermediate 2

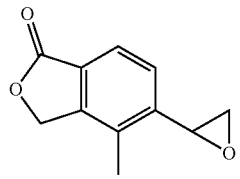

4-Methyl-5-oxiran-2-yl-2-benzofuran-1(3H)-one

Step A: 5-Ethenyl-4-methyl-2-benzofuran-1(3H)-one

5-Bromo-4-methyl-2-benzofuran-1(3H)-one (600 mg, 4.5 mmol), potassium vinyl trifluoroborate (510 mg, 2.2 mmmol), PdCl$_2$(dppf)-CH$_2$Cl$_2$ Adduct (180 mg, 0.220 mmmol), and TEA (0.62 mL, 4.5 mmol) were added to 10 mL ethanol in a 20 mL microwave tube. The tube was sealed and degassed, and then heated to 140° C. for 20 minutes. Analysis by LC-MS showed product peak. The reaction mixture was diluted with ethyl acetate, washed with brine twice, and dried and evaporated to dryness. The crude product was purified by MPLC chromatography (0-80% ETOAC/Hexane solvent system) to yield 5-ethenyl-4-methyl-2-benzofuran-1(3H)-one.
$^1$H-NMR (500 MHz, CDCl$_3$): δ ppm 7.76 (d, J=8 Hz, 1H), 7.03 (dd, J=11, 17 Hz, 1H), 5.84 (d, J=17 Hz, 1H), 5.55 (d, J=11 Hz, 1H), 5.29 (s, 2H), 2.34 (s, 3H). LC-MS: [M+1]=175.

Step B: 4-Methyl-5-oxiran-2-yl-2-benzofuran-1(3H)-one 5-ethenyl-4-methyl-2-benzofuran-1(3H)-one (1.5 g, 8.4 mmol) was added to DCM (25 mL) at 0° C. then meta-chloroperbenzoic acid (2.9 g, 17 mmol) was added and the mixture was stirred at room temperature overnight. The reaction mixture was washed once each with saturated aqueous Na$_2$S$_2$O$_3$, saturated sodium bicarbonate, and brine. The organic layer was dried over Na$_2$SO$_4$, filtered, and evaporated to dryness. The crude material was purified by MPLC chromatography (eluting with 0-80% EtOAc/hexane solvent system) to yield 4-methyl-5-oxiran-2-yl-2-benzofuran-1(3H)-one.
$^1$H-NMR (500 MHz, CDCl$_3$): δ ppm 7.77 (d, J=8 Hz, 1H), 7.43 (d, J=8 Hz, 1H), 5.30 (s, 2H), 4.12 (s, 1H), 3.27 (t, J=4 Hz, 1H), 2.74 (dd, J=2.2, 5.5 Hz, 1H), 2.43 (s, 3H).
LC-MS: [M+1]=191.

Intermediates 2A and 2B

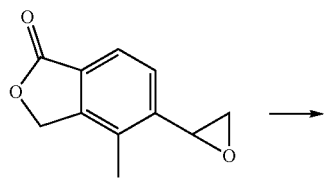

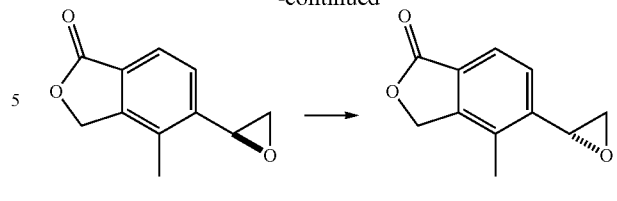

Slow eluting 2A      Fast eluting 2B

2A: 4-Methyl-5-[(2R)-oxiran-2-yl]-2-benzofuran-1(3H)-one

2B: 4-Methyl-5-[(2R)-oxiran-2-yl]-2-benzofuran-1(3H)-one

Racemic 4-methyl-5-oxiran-2-yl-2-benzofuran-1(3H)-one was resolved on a ChiralPak® AD-H column (5×25 cm) under supercritical fluid chromatography (SFC) conditions on a Berger MGIII preparative SFC instrument. The racemate was diluted to 50 mg/ml in 1:1 DCM:MeOH. The separation was accomplished using 10% EtOH/CO2, flow rate 200 ml/min, 100 bar, 25° C. 500 μl Injections were spaced every 2.12 minutes. The fast epoxide (4-methyl-5-[(2R)-oxiran-2-yl]-2-benzofuran-1(3H)-one, 3B) eluted at 5.2 minutes, and the slow epoxide (4-methyl-5-[(2R)-oxiran-2-yl]-2-benzofuran-1(3H)-one, 3A) eluted at 5.6 minutes.

Alternatively, the resolution could also be achieved using a mobile phase of 8% MeOH 98% CO$_2$ with a flow rate of 100 ml minute. In that case the sample was prepared by dissolving in methanol, 20 mg/ml, and using a 1 mL volume per injection. After separation, the fractions were dried off via rotary evaporator at bath temperature 40° C.

The absolute stereochemistry of each enantiomer was inferred based on the X-ray crystal structure determination of a derivative made with 2B, and by Mosher ester and Trost ester $^1$HNMR analysis of an ester made starting from 2B. The B epoxide isomer finds utility in the present invention.

Intermediate 2B

Method 2

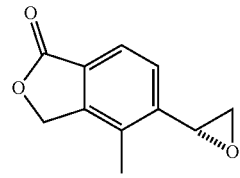

4-methyl-5-[(2R)-oxiran-2-yl]-2-benzofuran-1(3H)-one

Step A: 3-hydroxymethyl-2-methyl phenol

To a 5 L 3 neck RB flask equipped with overhead stirrer was charged NaBH$_4$ (87.0 g, 2.30 mol) and THF (3.0 L), and the resulting slurry was cooled to 10° C. To the slurry was then added 3-hydroxy-2-methyl benzoic acid (175 g, 1.15 mol) portionwise over 20 minutes (Tmax 17° C.). A stirrable slurry formed, and was aged for an additional 45 minutes at 10-15°

C. after which BF$_3$—OEt$_2$ (321 mL, 2.53 mol) was added slowly over 1.5 hours. The slurry was aged at 10° C.-15° C. for 2 hours and then assayed for reaction completion (98.5% conversion). The slurry was cooled to <10° C. and quenched with 931 mL MeOH slowly over 1.5 h (gas evolution). The resulting slurry was aged overnight at room temperature. The batch was cooled to <10° C. then quenched with 1 N HCl (1.5 L) to get a homogeneous solution (pH solution 1), which was aged for 30 minutes and then the organic solvents were removed by rotary evaporation to approximately 1.8 L of total reaction volume (bath temperature was set to 50° C.; internal temp of concentrate after rotary evaporation was 40° C.). The slurry was held at 45° C. for 30 minutes and then cooled slowly to 15° C. The solids were filtered and washed with cold (15° C.) water (2×300 mL), providing 3-hydroxymethyl-2-methyl phenol.

$^1$H-NMR (400 MHz, DMSO-d$_6$): δ 9.11 (s, 1H), 6.95 (t, J=7.8 Hz, 1H), 6.82 (d, J=7.4 Hz, 1H), 6.71 (d, J=7.8 Hz, 1H), 4.93 (t, J=5.5 Hz, 1H), 4.44 (d, J=5.5 Hz, 2H), 2.06 (s, 3H).

Step B: 4-Bromo-3-hydroxymethyl-2-methyl phenol

3-Hydroxymethyl-2-methyl phenol (113.9 g, 824.0 mmol) was dissolved in a mixture of acetonitrile (850 mL) and trifluoroacetic acid (750.0 mL, 9,735 mmol) in a 3-neck 5-L flask under nitrogen. The reaction mixture was cooled to −33° C. N-bromosuccinimide (141 g, 791 mmol) was added over 15 minutes, with the temperature during addition in the range of −35 to −33° C. The reaction mixture was allowed to stir for an additional 15 minutes during which time the temperature decreased to −40° C. The cooling bath was removed, and potassium carbonate (741.0 g, 5,358 mmol) diluted with water to a total of 1.0 L was added. Off-gassing was observed, and the temperature increased to 25° C. MTBE (1.5 L) was added, and the reaction mixture was transferred to a separatory funnel. The layers were separated. The aqueous layer was diluted with water (500 mL) and extracted with MTBE (1 L)+EtOAc (500 mL), and then MTBE (500 mL)+EtOAc (250 mL). The combined organic layers were washed with water (240 mL) and dried over sodium sulfate. The sodium sulfate was removed by filtration, washed with additional MTBE and concentrated under reduced pressure. MTBE (684 mL, 2 volumes) was added, and the suspension was heated to 40° C. to produce a homogeneous solution. The solution was allowed to cool to room temperature. Six volumes of heptane were added, and the suspension was stirred overnight. The suspension was filtered, and the crystals were washed with 4:1 heptane: MTBE (500 mL), followed by heptane (500 mL). The solid was dried under vacuum, providing 4-bromo-3-hydroxymethyl-2-methyl phenol.

$^1$H NMR (400 MHz, DMSO-d$_6$): δ 9.52 (s, 1H), 7.21 (d, J=8.6 Hz, 1H), 6.71 (d, J=8.6 Hz, 1H), 4.88 (t, J=5.1 Hz, 1H), 4.59 (d, J=5.1 Hz, 2H), 2.23 (s, 3H)

Step C:
5-Hydroxy-4-methyl-3H-isobenzofuran-1-one

To a 2 L 3 neck flask equipped with overhead stirrer, N$_2$ inlet, and condenser were charged 4-bromo-3-hydroxymethyl-2-methyl phenol (100 g, 461 mmol), CuCN (83.0 g, 921 mmol), and DMF (500 mL). The solution was sparged with N$_2$ for 15 minutes and then heated to 145° C. to obtain a homogeneous solution. The solution was aged at 145° C. for 2 hours, and then the reaction mixture was cooled to 95° C. 41.5 mL water was added (sparged with N$_2$), and the reaction aged for 20 hours. The reaction was cooled to room temperature, the solids filtered through Solka-Flok® powdered cellulose and the cake washed with 50 mL DMF. To a 3 L flask containing 1 L EtOAc was added the DMF filtrate. A precipitate coating formed in bottom of flask. The DMF/EtOAc suspension was filtered through Solka-Flok® and the cake was washed with 250 mL EtOAc. The resulting filtrate was washed with 5% brine solution (3×500 mL). The aqueous layers were extracted with 500 mL EtOAc and the combined organics were dried over MgSO$_4$, filtered and evaporated. The solids were slurried in 250 mL MTBE at room temperature, and then filtered and washed with 100 mL MTBE. The solids were dried under vacuum at room temperature, providing 5-hydroxy-4-methyl-3H-isobenzofuran-1-one.

$^1$H NMR (400 MHz, DMSO-d$_6$): δ 10.52 (s, 1H), 7.51 (d, J=8.3 Hz, 1H), 6.99 (d, J=8.3 Hz, 1H), 5.28 (s, 2H), 2.07 (s, 3H).

Step D: Trifluoromethanesulfonic acid
4-methyl-1-oxo-1,3-dihydro-isobenzofuran-5-yl
ester 5-Hydroxy-4-methyl-3H-isobenzofuran-1-one (46.8 g, 285 mmol) was suspended in dichloromethane (935 mL) in 2-L roundbottom flask equipped with overhead stirrer under nitrogen. Triethylamine (59.5 mL, 427 mmol) was added, and the reaction mixture was cooled in an ice bath to 3.8° C. Trifluoromethanesulfonic anhydride (67.4 mL, 399 mmol) was added via addition funnel over 50 minutes, keeping the temperature <10° C. After stirring the reaction mixture for an additional 15 minutes, the reaction mixture was quenched with water (200 mL), and then stirred with DARCO® KB (activated carbon, 25 g) for 15 minutes. The biphasic mixture was filtered over Solka-Floc®, washing with additional dichloromethane, and transferred to a separatory funnel, whereupon it was diluted with additional water (300 mL). The layers were separated, and the organic layer was washed with water (500 mL) and 10% brine (200 mL). The dichloromethane solution was dried over sodium sulfate, filtered and evaporated. The orange-red solid was adsorbed onto silica gel (27.5 g) and eluted through a pad of silica gel (271 g) with 25% ethyl acetate/hexanes. The resulting solution was concentrated under vacuum with the product crystallizing during concentration. The suspension was filtered, and the solid was washed with heptane and dried under vacuum and nitrogen, providing trifluoromethanesulfonic acid 4-methyl-1-oxo-1,3-dihydro-isobenzofuran-5-yl ester.

$^1$H NMR (400 MHz, CDCl$_3$): δ 7.87 (d, J=8.4 Hz, 1H), 7.47 (d, J=8.4 Hz, 1H), 5.32 (s, 2H), 2.41 (s, 3H).

Step E: 5-(1-Butoxy-vinyl)-4-methyl-3H-isobenzofuran-1-one

To a 1 L 3-neck was charged trifluoromethanesulfonic acid, 4-methyl-1-oxo-1,3-dihydro-isobenzofuran-5-yl ester (63.0 g, 213 mmol), DMF (315 mL), butyl vinyl ether (138 mL, 1063 mmol)), and then Et$_3$N (35.6 mL, 255 mmol). The solution was sparged with N$_2$ for 20 minutes. To the solution was added Pd(OAc)$_2$ (1.19 g, 5.32 mmol) and DPPP (2.41 g, 5.85 mmol), and the solution was then sparged for an additional 10 minutes, and then heated to 80° C. After a 1 hour age, the solution was cooled to <10° C., quenched with 630 mL EtOAc, and then washed with 5% NH$_4$Cl (2×315 mL) and 10% brine (2×315 mL). The solution was then dried over MgSO$_4$, filtered, concentrated by rotary evaporation and flushed with EtOAc (3×100 mL) to remove excess butyl vinyl ether, providing crude 5-(1-butoxy-vinyl)-4-methyl-3H-isobenzofuran-1-one.

$^1$H NMR (400 MHz, DMSO-d$_6$): δ 7.67 (d, J=7.7 Hz, 1H), 7.48 (d, J=7.7 Hz, 1H), 5.42 (s, 2H), 4.54 (d, J=2.3 Hz, 1H), 4.27 (d, J=2.3 Hz, 1H), 3.85 (t, J=6.4 Hz, 2H), 2.27 (s, 3H), 1.71-1.64 (m, 2H), 1.46-1.37 (m, 2H), 0.92 (t, J=7.4 Hz, 3H).

Step F: 5-(2-Bromo-acetyl)-4-methyl-3H-isobenzofuran-1-one

To a 1 L 3-neck flask equipped with overhead stirrer was added crude 5-(1-butoxy-vinyl)-4-methyl-3H-isobenzofuran-1-one (55.8 g) and THF (315 mL). The solution was cooled to <5° C. after which water (79 mL) was added and the solution was maintained at <5° C. NBS (41.6 g) was then added portionwise while maintaining Tmax=19° C. The solution was then warmed to room temperature for 30 minutes. HBr (48%, 0.241 mL) was added and the reaction was aged at room temperature for approximately 1 hour after which 236 mL water was then added to the batch. A water bath was used to maintain temp at 20° C. Another 315 mL of water was added (solvent composition 1:2 THF:water) and the slurry was cooled to 15° C. The resulting solids were filtered and washed with a cold 1:2 THF:water (15° C.): 150 mL displacement wash followed by 100 mL slurry wash. The solids were dried under vacuum at room temperature to provide 5-(2-bromo-acetyl)-4-methyl-3H-isobenzofuran-1-one.

$^1$H NMR (400 MHz, DMSO-d$_6$): δ 7.99 (d, J=7.8 Hz, 1H), 7.82 (d, J=7.8 Hz, 1H), 5.49 (s, 2H), 4.92 (s, 2H), 2.33 (s, 3H).

Step G: 4-methyl-5-[(2R)-oxiran-2-yl]-2-benzofuran-1(3H)-one 5-(2-Bromo-acetyl)-4-methyl-3H-isobenzofuran-1-one (48.8 g, 181 mmol) was charged to a 5 L 3 neck round bottom equipped with overhead stirrer, thermocouple, and heating mantle. 2-Propanol (1.22 L) was added, followed by 610 mL of pH 7.1M potassium phosphate buffer. Buffer solution (610 mL) was charged to a 1.0 L Erlenmeyer flask, and 2.44 g of NADP was added to the Erlenmeyer flask and swirled to dissolve. A reducing enzyme, KRED MIF-20 (2.44 g) (available from Codexis, Inc., 200 Penobscot Drive, Redwood City, Calif. 94063, www.codexis.com, tel. 1-650-421-8100) was added to the Erlenmeyer flask and the mixture was swirled to dissolve the solids. The resulting solution was added to the 5 L round bottom, which was then heated to 28° C. and aged for 6 hours, at which point the reaction was cooled to room temperature, and triethylamine (50.2 mL, 360 mmol) was added. The resulting solution was aged at 40° C. for 1 hour. The light slurry solution was cooled to room temperature, after which 122 g NaCl was added. The solution was aged at room temperature and then extracted with 1.22 L isopropyl acetate (IPAc). The aqueous layer was re-extracted with 400 mL IPAc and the combined organics were washed with 400 mL 20% brine solution, dried over MgSO$_4$, filtered and concentrated by rotary evaporation. The resulting solids were taken up in 100 mL IPAc (thick slurry). Hexanes were added (400 mL) and the suspension aged at room temperature and then filtered and washed w 5:1 Hexanes:IPAc solution (150 mL). The crystalline solids were dried under vacuum at room temperature to provide 4-methyl-5-[(2R)-oxiran-2-yl]-2-benzofuran-1(3H)-one.

$^1$H NMR (400 MHz, CDCl$_3$): δ 7.75 (d, J=8.1 Hz, 1H), 7.42 (d, J=8.1 Hz, 1H), 5.28 (s, 2H), 4.10 (dd, J=4.0, 2.8, 1H), 3.26 (dd, J=5.6, 4.0, 1H), 2.72 (dd, J=5.6, 2.8, 1H), 2.42 (s, 3H).

Intermediate 3

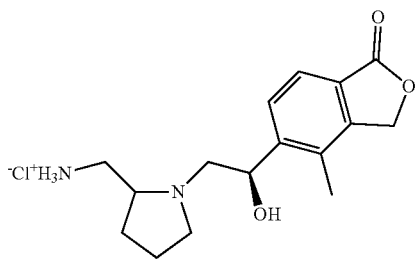

5-[(1R)-2-[2-(Aminomethyl)pyrrolidin-1-yl]-1-hydroxyethyl}-4-methyl-2-benzofuran-1(3H)-one hydrochloride Step A: tert-Butyl({1-[(2R)-2-hydroxy-2-(4-methyl-1-oxo-1,3-dihydro-2-benzofuran-5-yl)ethyl]pyrrolidin-2-yl}methyl)carbamate Six vials containing a solution of 4-methyl-5-[(2R)-oxiran-2-yl]-2-benzofuran-1(3H)-one (325 mg, 1.67 mmol) in 12 mL ethanol added to tert-butyl(pyrrolidin-2-ylmethyl)carbamate (333 mg, 1.67 mmol) were prepared. The reaction mixtures were microwaved at 140° C. for 55 minutes. The solutions were combined and the solvents were removed in vacuo. The resulting residue was purified by HPLC to afford two diastereomers of tert-butyl({1-[(2R)-2-hydroxy-2-(4-methyl-1-oxo-1,3-dihydro-2-benzofuran-5-yl)ethyl]pyrrolidin-2-yl}methyl)carbamate:

Faster eluting diastereomer: LC-MS (IE, m/z): 391 [M+1]$^+$.

Slower eluting diastereomer: LC-MS (IE, m/z): 391 [M+1]$^+$.

Step B: 5-{(1R)-2-[2-(Aminomethyl)pyrrolidin-1-yl]-1-hydroxyethyl}-4-methyl-2-benzofuran-1(3H)-one A suspension of the faster eluting diastereomer of tert-butyl({1-[(2R)-2-hydroxy-2-(4-methyl-1-oxo-1,3-dihydro-2-benzofuran-5-yl)ethyl]pyrrolidin-2-yl}methyl)carbamate (710 mg, 1.82 mmol) in dioxane (2.0 mL) was treated with a solution of hydrochloric acid in dioxane (4.0 M, 2.0 mL). After shaking sixteen hours, the solvents were removed in vacuo to provide 5-[(1R)-2-[2-(aminomethyl)pyrrolidin-1-yl]-1-hydroxyethyl}-4-methyl-2-benzofuran-1(3H)-one hydrochloride which was carried on without purification.

LC-MS (IE, m/z): 291 [M+1]$^+$.

Intermediate 4

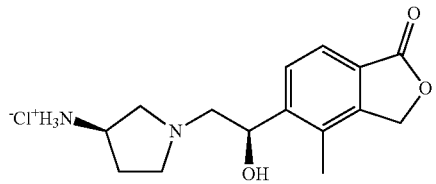

5-{(1R)-2-[(3R)-3-Aminopyrrolidin-1-yl]-1-hydroxyethyl}-4-methyl-2-benzofuran-1(3H)-one hydrochloride 5-{(1R)-2-[(3R)-3-Aminopyrrolidin-1-yl]-1-hydroxyethyl}-4-methyl-2-benzofuran-1(3H)-one hydrochloride was prepared in a similar fashion to that described for the synthesis of INTERMEDIATE 3 starting from tert-butyl(3R)-3-aminopyrrolidine-1-carboxylate and 4-methyl-5-[(2R)-oxiran-2-yl]-2-benzofuran-1(3H)-one [INTERMEDIATE 2B].

LC-MS (IE, m/z): 313 [M+1]⁺.

Intermediate 5

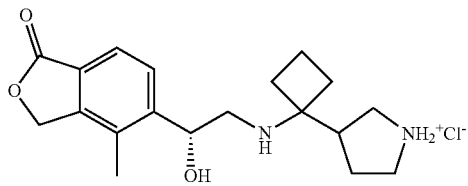

5-[(1R)-1-Hydroxy-2-{[1-(pyrrolidin-3-yl)cyclobutyl]amino}ethyl]-4-methyl-2-benzofuran-1(3H)-one hydrochloride 5-[(1R)-1-Hydroxy-2-{[1-(pyrrolidin-3-yl)cyclobutyl]amino}ethyl]-4-methyl-2-benzofuran-1(3H)-one hydrochloride was prepared in a similar fashion to that described for the synthesis of INTERMEDIATE 3 starting from commercially available tert-butyl 3-(1-aminocyclobutyl)pyrrolidine-1-carboxylate and 4-methyl-5-[(2R)-oxiran-2-yl]-2-benzofuran-1(3H)-one [INTERMEDIATE 2B].

LC-MS (IE, m/z): 331 [M+1]⁺.

Intermediate 6

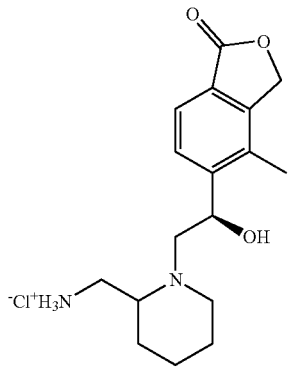

5-[(1R)-2-[2-(Aminomethyl)piperidin-1-yl]-1-hydroxyethyl}-4-methyl-2-benzofuran-1(3H)-one hydrochloride 5-[(1R)-2-[2-(Aminomethyl)piperidin-1-yl]-1-hydroxyethyl}-4-methyl-2-benzofuran-1(3H)-one hydrochloride was prepared in a similar fashion to that described for the synthesis of INTERMEDIATE 3 starting from tert-butyl(piperidin-2-ylmethyl)carbamate and 4-methyl-5-[(2R)-oxiran-2-yl]-2-benzofuran-1(3H)-one [INTERMEDIATE 2B].

LC-MS (IE, m/z): 305 [M+1]⁺.

Intermediate 7

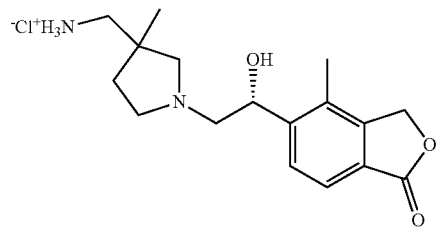

5-[(R)-2-[3-(Aminomethyl)-3-methylpyrrolidin-1-yl]-1-hydroxyethyl}-4-methyl-2-benzofuran-1(3H)-one hydrochloride 5-[(R)-2-[3-(Aminomethyl)-3-methylpyrrolidin-1-yl]-1-hydroxyethyl}-4-methyl-2-benzofuran-1(3H)-one hydrochloride was prepared in a similar fashion to that described for the synthesis of INTERMEDIATE 3 starting from commercially available tert-butyl[(3-methylpyrrolidin-3-yl)methyl]carbamate and 4-methyl-5-[(2R)-oxiran-2-yl]-2-benzofuran-1(3H)-one [INTERMEDIATE 2B].

LC-MS (IE, m/z): 305 [M+1]⁺.

Intermediate 8

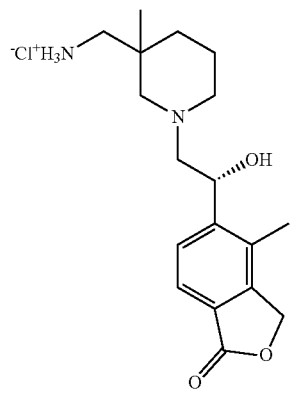

5-[(R)-2-[3-(Aminomethyl)-3-methylpiperidin-1-yl]-1-hydroxyethyl}-4-methyl-2-benzofuran1(3H)-one hydrochloride 5-[(R)-2-[3-(Aminomethyl)-3-methylpiperidin-1-yl]-1-hydroxyethyl}-4-methyl-2-benzofuran1(3H)-one hydrochloride was prepared in a similar fashion to that described for the synthesis of INTERMEDIATE 3 starting from commercially available tert-butyl[(3-methylpiperidin-3-yl)methyl]carbamate and 4-methyl-5-[(2R)-oxiran-2-yl]-2-benzofuran-1(3H)-one [INTERMEDIATE 2B].

LC-MS (IE, m/z): 319 [M+1]⁺.

Intermediate 9 A and B

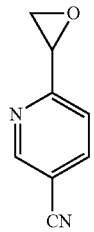

6-(Oxiran-2-yl) pyridine-3-carbonitrile

Step A: 6-Ethenylpyridine-3-carbonitrile

To a stirring solution of 6-bromopyridine-3-carbonitrile (2.0 g, 10.9 mmol), in EtOH (70 mL) were added bis[(diphenylphosphino)ferrocene]dichloropalladium(II) complex with dichloromethane (0.892 mg, 0.10 mmol), potassium vinyl trifluoroborate (2.93 g, 21.9 mmol), triethylamine (3.0 mL, 21.9 mmol), and water (0.5 mL). The reaction mixture was heated to reflux. Upon completion as determined by reverse phase HPLC-MS (1-2 h) and TLC (eluent: 10% ethyl acetate in hexanes), the reaction was cooled to room temperature, and then was diluted with water and extracted with EtOAc. The combined organic layers were washed with brine and dried over MgSO$_4$. The extracts were concentrated and chromatographed over a column of SiO$_2$ (0-20% EtOAc hexanes as eluent). Evaporation of the solvent yielded 6-ethenylpyridine-3-carbonitrile.

$^1$H NMR (500 MHz, CDCl$_3$), δ 8.85 (s, 1H), 7.94-7.93 (m, 1H), 6.89-6.83 (m, 1H), 7.45 (d, J=8.2 Hz, 1H), 6.85 (dd, J=10.8, Hz, 1H), 6.42 (d, J=17.4 Hz, 1H); LCMS (M+1)$^+$=131.

Step B: 6-(Oxiran-2-yl) pyridine-3-carbonitrile

A solution of 6-ethenylpyridine-3-carbonitrile (0.742 g, 5.70 mmol) in a 2:1 ratio of H$_2$O:t-BuOH (30 mL) was treated with N-bromosuccinimide in portions over 5 minutes (1.07 g, 5.99 mmol) and stirred at 40° C. for 1 hour. After cooling to 5° C., the reaction was basified with drop wise addition of a solution of sodium hydroxide (0.684 g in 5 mL of H$_2$O, 17.1 mmol) and stirred for another 1 hour. The reaction mixture was poured into H$_2$O (10 mL) and extracted with EtOAc (2×50 mL). The combined organic layers were washed with saturated aqueous NaCl (1×30 mL) and dried over MgSO$_4$. Evaporation of the solvent and purification over SiO$_2$ (0-30% EtOAc hexanes as eluent) provided 6-(oxiran-2-yl) pyridine-3-carbonitrile.

$^1$H NMR (500 MHz, CDCl$_3$), δ 8.87 (s, 1H), 7.99 (d, J=8.1 Hz, 1H), 7.40 (d, J=8.1 Hz, 1H), 4.11 (s, 1H), 4.08 (dd, J=2.6 Hz, J=2.3 Hz, 1H), 3.29 (m, 1H), 2.94 (m, 1H); LCMS (M+1)$^+$=147.

Resolution of the epoxides was carried out (prep SFC, 160 mL/min., 10% MeOH in SC CO$_2$, AD-H) to provide:

Isomer A: (M+1)$^+$=147.
Isomer B: (M+1)$^+$=147.

Intermediate 10

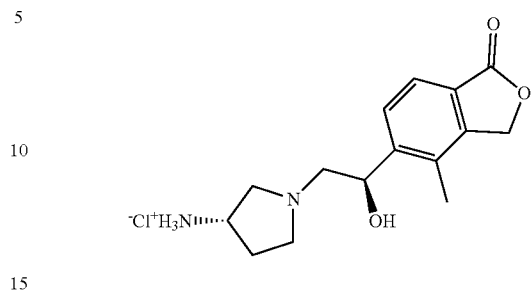

5-{(1R)-2-[(3S)-3-Aminopyrrolidin-1-yl]-1-hydroxyethyl}-4-methyl-2-benzofuran-1(3H)-one hydrochloride 5-{(1R)-2-[(3S)-3-Aminopyrrolidin-1-yl]-1-hydroxyethyl}-4-methyl-2-benzofuran-1(3H)-one hydrochloride was prepared in a similar fashion to that described for the synthesis of INTERMEDIATE 3 starting from tert-butyl(3S)-pyrrolidin-3-ylcarbamate and 4-methyl-5-[(2R)-oxiran-2-yl]-2-benzofuran-1(3H)-one [INTERMEDIATE 2B].

LC-MS (IE, m/z): 277 [M+1]$^+$.

Intermediate 11

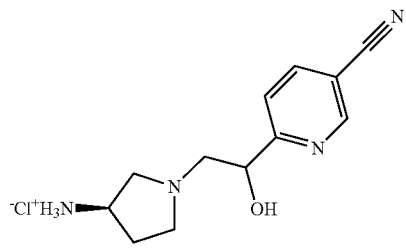

6-{2-[(3R)-3-Aminopyrrolidin-1-yl]-1-hydroxyethyl}pyridine-3-carbonitrile hydrochloride 6-{2-[(3R)-3-Aminopyrrolidin-1-yl]-1-hydroxyethyl}pyridine-3-carbonitrile hydrochloride was prepared in a similar fashion to that described for the synthesis of INTERMEDIATE 3 starting from tert-butyl(3R)-pyrrolidin-3-ylcarbamate and the slower eluting isomer of 6-(oxiran-2-yl) pyridine-3-carbonitrile (INTERMEDIATE 9 B).

LC-MS (IE, m/z): 233 [M+1]$^+$.

Intermediate 12

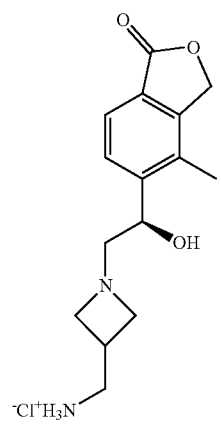

(R)-5-(2-(3-(Aminomethyl)azetidin-1-yl)-1-hydroxy-ethyl)-4-methylisobenzofuran-1(3H)-one hydrochloride (R)-5-(2-(3-(Aminomethyl)azetidin-1-yl)-1-hydroxyethyl)-4-methylisobenzofuran-1(3H)-one hydrochloride was prepared in a similar fashion to that described for the synthesis of INTERMEDIATE 3 starting from tert-butyl azetidin-3-ylmethylcarbamate and 4-methyl-5-[(2R)-oxiran-2-yl]-2-benzofuran-1(3H)-one [INTERMEDIATE 2B].

LC-MS (IE, m/z): 277 [M+1]$^+$.

Intermediate 13

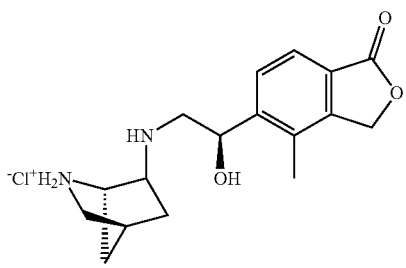

5-((1R)-2-((6S)-2-Azabicyclo[2.2.1]heptan-6-ylamino)-1-hydroxyethyl)-4-methylisobenzofuran-1(3H)-one hydrochloride 5-((1R)-2-((6S)-2-Azabicyclo[2.2.1]heptan-6-ylamino)-1-hydroxyethyl)-4-methylisobenzofuran-1(3H)-one hydrochloride was prepared in a similar fashion to that described for the synthesis of INTERMEDIATE 3 starting from commercially available (6S)-tert-butyl 6-amino-2-azabicyclo[2.2.1]heptane-2-carboxylate and 4-methyl-5-[(2R)-oxiran-2-yl]-2-benzofuran-1(3H)-one [INTERMEDIATE 2B].

LC-MS (IE, m/z): 303 [M+1]$^+$.

Intermediate 14

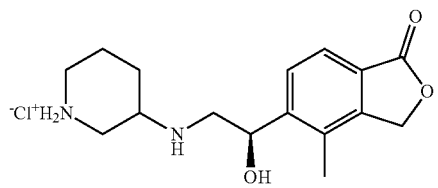

5-((1R)-1-Hydroxy-2-(piperidin-3-ylamino)ethyl)-4-methylisobenzofuran-1(3H)-one hydrochloride 5-((1R)-1-Hydroxy-2-(piperidin-3-ylamino)ethyl)-4-methylisobenzofuran-1(3H)-one hydrochloride was prepared in a similar fashion to that described for the synthesis of INTERMEDIATE 3 starting from tert-butyl 3-aminopiperidine-1-carboxylate and 4-methyl-5-[(2R)-oxiran-2-yl]-2-benzofuran-1(3H)-one [INTERMEDIATE 2B].

LC-MS (IE, m/z): 291 [M+1]$^+$.

Intermediate 15

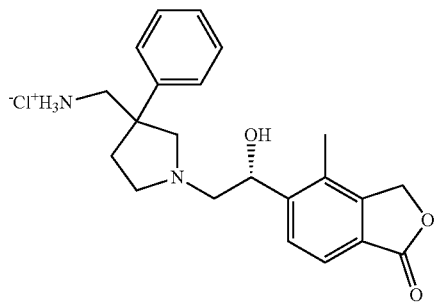

5-[(R)-2-[3-(Aminomethyl)-3-phenylpyrrolidin-1-yl]-1-hydroxyethyl}-4-methyl-2-benzofuran-1(3H)-one Hydrochloride 5-[(R)-2-[3-(Aminomethyl)-3-phenylpyrrolidin-1-yl]-1-hydroxyethyl}-4-methyl-2-benzofuran-1(3H)-one hydrochloride was prepared in a similar fashion to that described for the synthesis of INTERMEDIATE 3 starting from commercially available tert-butyl[(3-methylpyrrolidin-3-yl)methyl]carbamate and 4-methyl-5-[(2R)-oxiran-2-yl]-2-benzofuran-1(3H)-one [INTERMEDIATE 2B].

LC-MS (IE, m/z): 367 [M+1]$^+$.

Example 1

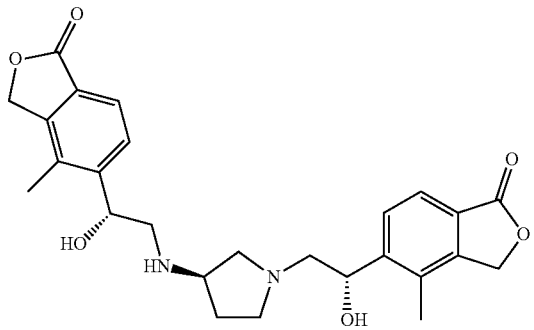 [SMILES: Cc1c([C@H](O)CN2CC[C@@H](NC[C@H](O)c3ccc4c(c3C)COC4=O)C2)ccc2c1COC2=O]

5-{(1R)-1-Hydroxy-2-[(3R)-3-{[(2R)-2-hydroxy-2-(4-methyl-1-oxo-1,3-dihydro-2-benzofuran-5-yl)ethyl]amino}pyrrolidin-1-yl]ethyl}-4-methyl-2-benzofuran-1(3H)-one A microwave vial was charged with 5-{(1R)-2-[(3R)-3-aminopyrrolidin-1-yl]-1-hydroxyethyl}-4-methyl-2-benzofuran-1(3H)-one hydrochloride [INTERMEDIATE 4] (100 mg, 0.32 mmol), 4-methyl-5-[(2R)-oxiran-2-yl]-2-benzofuran-1(3H)-one [INTERMEDIATE 2B] (61 mg, 0.32 mmol), MP-carbonate resin (200 mg), and ethanol (1 mL). The reaction mixture was heated in a microwave reactor at 150 C for 1 hour, and then cooled, filtered and concentrated in vacuo. The resulting residue was dissolved in DMSO (1 mL) and purified by HPLC to provide 5-{(1R)-1-hydroxy-2-[(3R)-3-{[(2R)-2-hydroxy-2-(4-methyl-1-oxo-1,3-dihydro-2-benzofuran-5-yl)ethyl]amino}pyrrolidin-1-yl]ethyl}-4-methyl-2-benzofuran-1(3H)-one.

LC-MS (IE, m/z): 467 [M+1]+.

Example 2

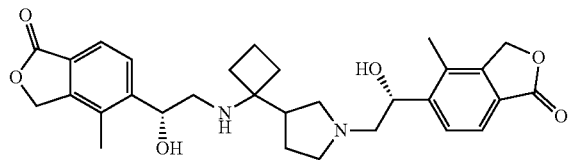 [SMILES: Cc1c([C@@H](O)CNC2(C3CCN(C[C@H](O)c4ccc5c(c4C)COC5=O)C3)CCC2)ccc2c1COC2=O]

5-{(1R)-1-Hydroxy-2-[3-(1-{[(2R)-2-hydroxy-2-(4-methyl-1-oxo-1,3-dihydro-2-benzofuran-5-yl)ethyl]amino}cyclobutyl)pyrrolidin-1-yl]ethyl}-4-methyl-2-benzofuran-1(3H)-one 5-{(1R)-1-Hydroxy-2-[3-(1-{[(2R)-2-hydroxy-2-(4-methyl-1-oxo-1,3-dihydro-2-benzofuran-5-yl)ethyl]amino}cyclobutyl)pyrrolidin-1-yl]ethyl}-4-methyl-2-benzofuran-1(3H)-one was prepared in a similar fashion to that described for the synthesis of EXAMPLE 1 starting from 5-[(1R)-1-hydroxy-2-{[1-(pyrrolidin-3-yl)cyclobutyl]amino}ethyl]-4-methyl-2-benzofuran-1(3H)-one hydrochloride [INTERMEDIATE 5] and 4-methyl-5-[(2R)-oxiran-2-yl]-2-benzofuran-1(3H)-one [INTERMEDIATE 2B].

LC-MS (IE, m/z): 521 [M+1]+.

Example 3

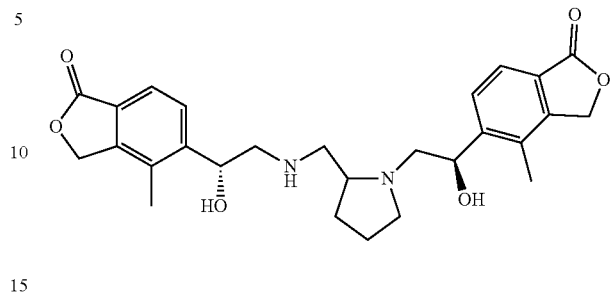

5-{(1R)-1-Hydroxy-2-[2-({[(2R)-2-hydroxy-2-(4-methyl-1-oxo-1,3-dihydro-2-benzofuran-5-yl)ethyl]amino}methyl)pyrrolidin-1-yl]ethyl}-4-methyl-2-benzofuran-1(3H)-one 5-{(1R)-1-Hydroxy-2-[2-({[(2R)-2-hydroxy-2-(4-methyl-1-oxo-1,3-dihydro-2-benzofuran-5-yl)ethyl]amino}methyl)pyrrolidin-1-yl]ethyl}-4-methyl-2-benzofuran-1(3H)-one (this is the correct name, OK) was prepared in a similar fashion to that described for the synthesis of EXAMPLE 1 starting from 5-[(1R)-2-[2-(aminomethyl)pyrrolidin-1-yl]-1-hydroxyethyl]-4-methyl-2-benzofuran-1(3H)-one hydrochloride [INTERMEDIATE 3] and 4-methyl-5-[(2R)-oxiran-2-yl]-2-benzofuran-1(3H)-one [INTERMEDIATE 2B].

LC-MS (IE, m/z): 481 [M+1]+.

Example 4

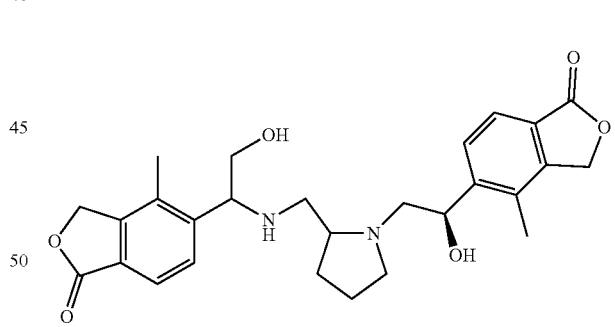

5-{(1R)-1-Hydroxy-2-[2-({[2-hydroxy-1-(4-methyl-1-oxo-1,3-dihydro-2-benzofuran-5-yl)ethyl]amino}methyl)pyrrolidin-1-yl]ethyl}-4-methyl-2-benzofuran-1(3H)-one 5-{(1R)-1-Hydroxy-2-[2-({[2-hydroxy-1-(4-methyl-1-oxo-1,3-dihydro-2-benzofuran-5-yl)ethyl]amino}methyl)pyrrolidin-1-yl]ethyl}-4-methyl-2-benzofuran-1(3H)-one was isolated as a minor diastereomer from the coupling reaction described in EXAMPLE 3.

LC-MS (IE, m/z): 481 [M+1]+.

Example 5

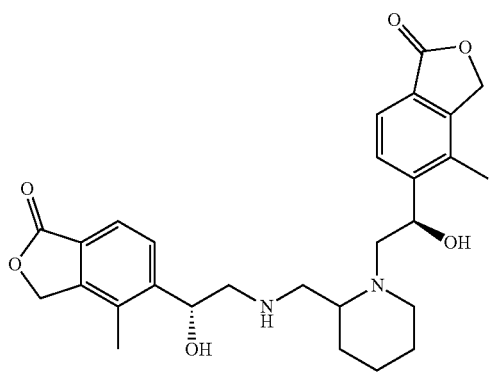 [SMILES: Cc1c([C@@H](O)CNCC2CCCCN2C[C@H](O)c2ccc3c(c2C)COC3=O)ccc2c1COC2=O]

5-{(1R)-1-Hydroxy-2-[2-({[(2R)-2-hydroxy-2-(4-methyl-1-oxo-1,3-dihydro-2-benzofuran-5-yl)ethyl]amino}methyl)piperidin-1-yl]ethyl}-4-methyl-2-benzofuran-1(3H)-one 5-{(1R)-1-Hydroxy-2-[2-({[(2R)-2-hydroxy-2-(4-methyl-1-oxo-1,3-dihydro-2-benzofuran-5-yl)ethyl]amino}methyl)piperidin-1-yl]ethyl}-4-methyl-2-benzofuran-1(3H)-one was prepared in a similar fashion to that described for the synthesis of EXAMPLE 1 starting from 5-[(1R)-2-[2-(Aminomethyl)piperidin-1-yl]-1-hydroxyethyl}-4-methyl-2-benzofuran-1(3H)-one hydrochloride [INTERMEDIATE 6] and 4-methyl-5-[(2R)-oxiran-2-yl]-2-benzofuran-1(3H)-one [INTERMEDIATE 2B].

LC-MS (IE, m/z): 495 [M+1]$^+$.

Example 6

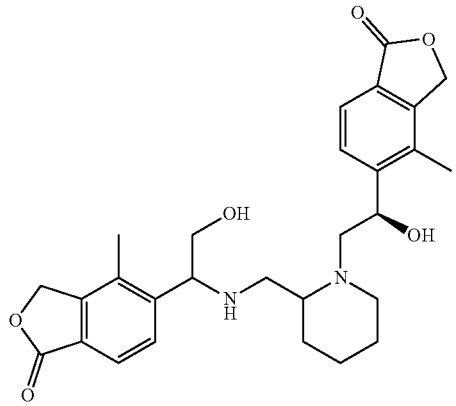 [SMILES: Cc1c(C(CO)NCC2CCCCN2C[C@H](O)c2ccc3c(c2C)COC3=O)ccc2c1COC2=O]

5-{(1R)-1-Hydroxy-2-[2-({[2-hydroxy-1-(4-methyl-1-oxo-1,3-dihydro-2-benzofuran-5-yl)ethyl]amino}methyl)piperidin-1-yl]ethyl}-4-methyl-2-benzofuran-1(3H)-one 5-{(1R)-1-Hydroxy-2-[2-({[2-hydroxy-1-(4-methyl-1-oxo-1,3-dihydro-2-benzofuran-5-yl)ethyl]amino}methyl)piperidin-1-yl]ethyl}-4-methyl-2-benzofuran-1(3H)-one was isolated as a minor diastereomer from the coupling reaction described in EXAMPLE 5.

LC-MS (IE, m/z): 495 [M+1]$^+$.

Example 7

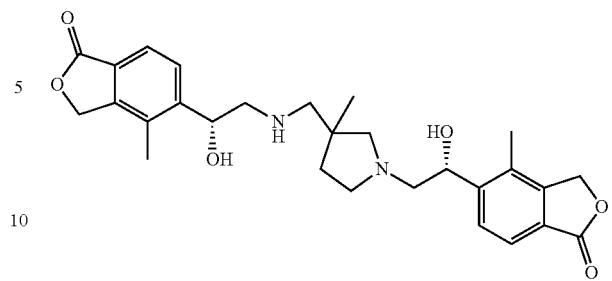

5-{(1R)-1-Hydroxy-2-[3-({[(2R)-2-hydroxy-2-(4-methyl-1-oxo-1,3-dihydro-2-benzofuran-5-yl)ethyl]amino}methyl)-3-methylpyrrolidin-1-yl]ethyl}-4-methyl-2-benzofuran-1(3H)-one 5-{(1R)-1-Hydroxy-2-[3-({[(2R)-2-hydroxy-2-(4-methyl-1-oxo-1,3-dihydro-2-benzofuran-5-yl)ethyl]amino}methyl)-3-methylpyrrolidin-1-yl]ethyl}-4-methyl-2-benzofuran-1(3H)-one was prepared in a similar fashion to that described for the synthesis of EXAMPLE 1 starting from 5-[(R)-2-[3-(aminomethyl)-3-methylpyrrolidin-1-yl]-1-hydroxyethyl]-4-methyl-2-benzofuran-1(3H)-one hydrochloride [INTERMEDIATE 7] and 4-methyl-5-[(2R)-oxiran-2-yl]-2-benzofuran-1(3H)-one [INTERMEDIATE 2B].

LC-MS (IE, m/z): 495 [M+1]$^+$.

Example 8

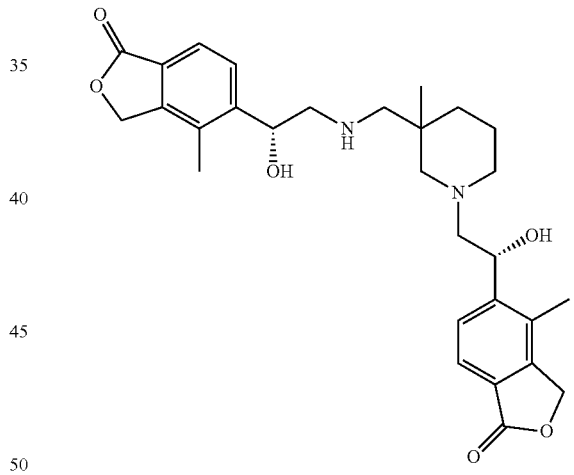

5-{(1R)-1-Hydroxy-2-[3-({[(2R)-2-hydroxy-2-(4-methyl-1-oxo-1,3-dihydro-2-benzofuran-5-yl)ethyl]amino}methyl)-3-methylpiperidin-1-yl]ethyl}-4-methyl-2-benzofuran-1(3H)-one 5-{(1R)-1-Hydroxy-2-[3-({[(2R)-2-hydroxy-2-(4-methyl-1-oxo-1,3-dihydro-2-benzofuran-5-yl)ethyl]amino}methyl)-3-methylpiperidin-1-yl]ethyl}-4-methyl-2-benzofuran-1(3H)-one was prepared in a similar fashion to that described for the synthesis of EXAMPLE 1 starting from 5-[(R)-2-[3-(aminomethyl)-3-methylpiperidin-1-yl]-1-hydroxyethyl]-4-methyl-2-benzofuran1(3H)-one hydrochloride [INTERMEDIATE 8] and 4-methyl-5-[(2R)-oxiran-2-yl]-2-benzofuran-1 (3H)-one [INTERMEDIATE 2B].

LC-MS (IE, m/z): 509 [M+1]$^+$.

Slower eluting diastereomer: LC-MS (IE, m/z): 449 [M+1]+.

Example 9 A and B

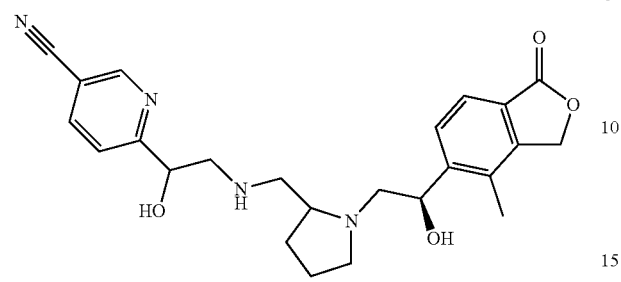

6-{1-Hydroxy-2-[({1-[(2R)-2-hydroxy-2-(4-methyl-1-oxo-1,3-dihydro-2-benzofuran-5-yl)ethyl]pyrrolidin-2-yl}methyl)amino]ethyl}pyridine-3-carbonitrile 6-{1-Hydroxy-2-[({1-[(2R)-2-hydroxy-2-(4-methyl-1-oxo-1,3-dihydro-2-benzofuran-5-yl)ethyl]pyrrolidin-2-yl}methyl)amino]ethyl}pyridine-3-carbonitrile was prepared in a similar fashion to that described for the synthesis of EXAMPLE 1 starting from 5-[(1R)-2-[2-(aminomethyl)pyrrolidin-1-yl]-1-hydroxyethyl]-4-methyl-2-benzofuran-1(3H)-one hydrochloride [INTERMEDIATE 3] and the slower eluting diastereomer of 6-(oxiran-2-yl) pyridine-3-carbonitrile (INTERMEDIATE 9 B).

Faster eluting diastereomer: LC-MS (IE, m/z): 437 [M+1]+.
Slower eluting diastereomer: LC-MS (IE, m/z): 437 [M+1]+.

Example 10

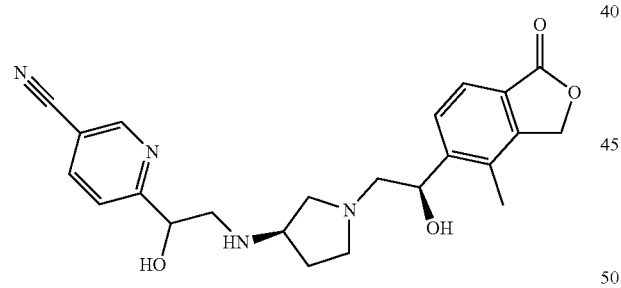

6-(1-Hydroxy-2-((R)-1-((R)-2-hydroxy-2-(4-methyl-1-oxo-1,3-dihydroisobenzofuran-5-yl)ethyl)pyrrolidin-3-ylamino)ethyl)nicotinonitrile 6-(1-Hydroxy-2-((R)-1-((R)-2-hydroxy-2-(4-methyl-1-oxo-1,3-dihydroisobenzofuran-5-yl)ethyl)pyrrolidin-3-ylamino)ethyl)nicotinonitrile was prepared in a similar fashion to that described for the synthesis of EXAMPLE 1 starting from 5-{(1R)-2-[(3R)-3-aminopyrrolidin-1-yl]-1-hydroxyethyl}-4-methyl-2-benzofuran-1(3H)-one hydrochloride [INTERMEDIATE 4] and the slower eluting diastereomer of 6-(oxiran-2-yl) pyridine-3-carbonitrile (INTERMEDIATE 9 B).

LC-MS (IE, m/z): 423 [M+1]+.

Example 11

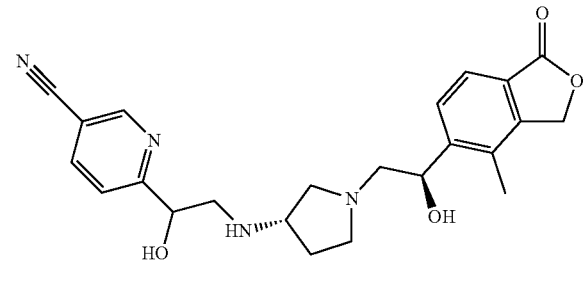 [SMILES: Cc1c([C@@H](O)CN2CC[C@H](NCC(O)c3ccc(C#N)cn3)C2)ccc2c1COC2=O]

6-(1-Hydroxy-2-((S)-1-((R)-2-hydroxy-2-(4-methyl-1-oxo-1,3-dihydroisobenzofuran-5-1)ethyl)nicotinonitrile 6-(1-Hydroxy-2-((S)-1-((R)-2-hydroxy-2-(4-methyl-1-oxo-1,3-dihydroisobenzofuran-5-yl)ethyl)pyrrolidin-3-ylamino)ethyl)nicotinonitrile was prepared in a similar fashion to that described for the synthesis of EXAMPLE 1 starting from 5-{(1R)-2-[(3S)-3-aminopyrrolidin-1-yl]-1-hydroxyethyl}-4-methyl-2-benzofuran-1(3H)-one hydrochloride [INTERMEDIATE 10] and the slower eluting diastereomer of 6-(oxiran-2-yl) pyridine-3-carbonitrile (INTERMEDIATE 9 B).

LC-MS (IE, m/z): 423 [M+1]+.

Example 12

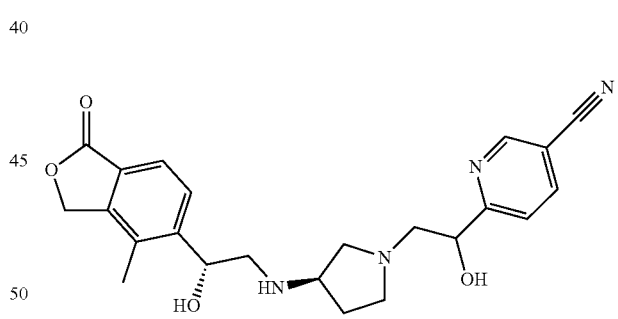

6-(1-Hydroxy-2-((R)-3-((R)-2-hydroxy-2-(4-methyl-1-oxo-1,3-dihydroisobenzofuran-5-yl)ethylamino)pyrrolidin-1-yl)ethyl)nicotinonitrile 6-(1-Hydroxy-2-((R)-3-((R)-2-hydroxy-2-(4-methyl-1-oxo-1,3-dihydroisobenzofuran-5-yl)ethylamino)pyrrolidin-1-yl)ethyl)nicotinonitrile was prepared in a similar fashion to that described for the synthesis of EXAMPLE 1 starting from 6-{2-[(3R)-3-aminopyrrolidin-1-yl]-1-hydroxyethyl}pyridine-3-carbonitrile hydrochloride [INTERMEDIATE 11] and 4-methyl-5-[(2R)-oxiran-2-yl]-2-benzofuran-1(3H)-one [INTERMEDIATE 2B].

LC-MS (IE, m/z): 423 [M+1]+.

Example 13

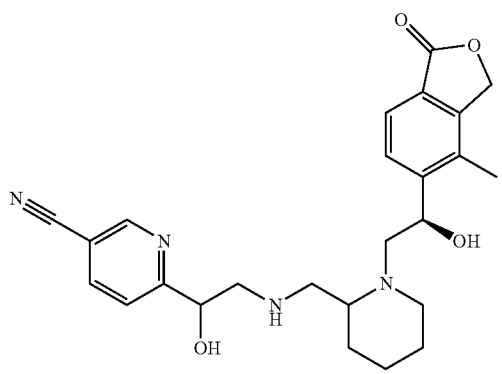 [SMILES: Cc1c([C@@H](O)CN2CCCCC2CNCC(O)c2ccc(C#N)cn2)ccc2c1COC2=O]

6-{1-Hydroxy-2-[({1-[(2R)-2-hydroxy-2-(4-methyl-1-oxo-1,3-dihydro-2-benzofuran-5-yl)ethyl]piperidin-2-yl}methyl)amino]ethyl}pyridine-3-carbonitrile 6-{1-Hydroxy-2-[({1-[(2R)-2-hydroxy-2-(4-methyl-1-oxo-1,3-dihydro-2-benzofuran-5-yl)ethyl]piperidin-2-yl}methyl)amino]ethyl}pyridine-3-carbonitrile was prepared in a similar fashion to that described for the synthesis of EXAMPLE 1 starting from 5-[(1R)-2-[2-(aminomethyl)piperidin-1-yl]-1-hydroxyethyl]-4-methyl-2-benzofuran-1(3H)-one hydrochloride [INTERMEDIATE 6] and the slower eluting diastereomer of 6-(oxiran-2-yl) pyridine-3-carbonitrile (INTERMEDIATE 9 B).

LC-MS (IE, m/z): 451 [M+1]⁺.

Example 14

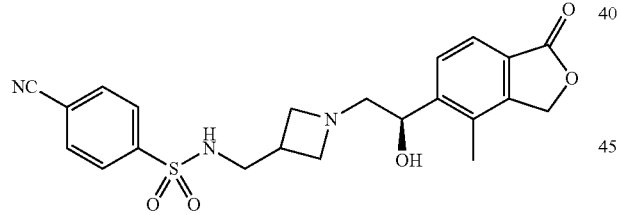

(R)-4-Cyano-N-((1-(2-hydroxy-2-(4-methyl-1-oxo-1,3-dihydroisobenzofuran-5-yl)ethyl)azetidin-3-yl)methyl)benzenesulfonamide To a vial containing (R)-5-(2-(3-(aminomethyl)azetidin-1-yl)-1-hydroxyethyl)-4-methylisobenzofuran-1(3H)-one hydrochloride [INTERMEDIATE 12] (0.17 g, 0.54 mmol) was added commercially available 4-cyanobenzene-1-sulfonyl chloride (0.20 g, 1.0 mmol) as a solution in DMF (500 μL) followed by diisopropylethylamine (0.16 g, 1.2 mmol). The vial was shaken for 24 hours, and then was concentrated in vacuo. The resulting residue was dissolved in DMSO (1 mL) and purified by HPLC to provide (R)-4-cyano-N-((1-(2-hydroxy-2-(4-methyl-1-oxo-1,3-dihydroisobenzofuran-5-yl)ethyl)azetidin-3-yl)methyl)benzenesulfonamide.

LC-MS (IE, m/z): 442 [M+1]

Example 15

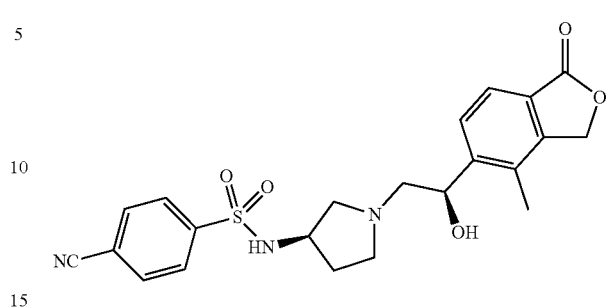

4-Cyano-N—((R)-1-((R)-2-hydroxy-2-(4-methyl-1-oxo-1,3-dihydroisobenzofuran-5-yl)ethyl)pyrrolidin-3-yl)benzenesulfonamide 4-Cyano-N—((R)-1-((R)-2-hydroxy-2-(4-methyl-1-oxo-1,3-dihydroisobenzofuran-5-yl)ethyl)pyrrolidin-3-yl)benzenesulfonamide was prepared in a similar fashion to that described for the synthesis of EXAMPLE 14 starting from 5-{(1R)-2-[(3R)-3-Aminopyrrolidin-1-yl]-1-hydroxyethyl}-4-methyl-2-benzofuran-1(3H)-one hydrochloride [INTERMEDIATE 4] and 4-cyanobenzene-1-sulfonyl chloride.

LC-MS (IE, m/z): 442 [M+1]

Example 16

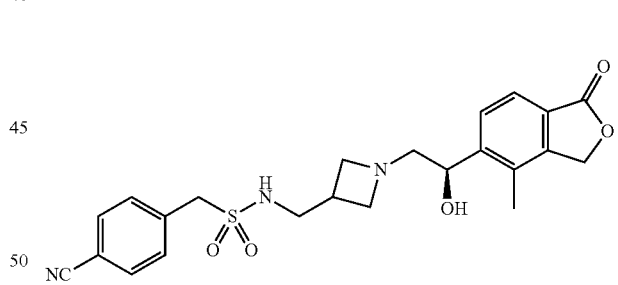

(R)-1-(4-Cyanophenyl)-N-((1-(2-hydroxy-2-(4-methyl-1-oxo-1,3-dihydroisobenzofuran-5-yl)ethyl)azetidin-3-yl)methyl)methanesulfonamide (R)-1-(4-Cyanophenyl)-N-((1-(2-hydroxy-2-(4-methyl-1-oxo-1,3-dihydroisobenzofuran-5-yl)ethyl)azetidin-3-yl)methyl)methanesulfonamide was prepared in a similar fashion to that described for the synthesis of EXAMPLE 14 starting from (R)-5-(2-(3-(aminomethyl)azetidin-1-yl)-1-hydroxyethyl)-4-methylisobenzofuran-1(3H)-one hydrochloride [INTERMEDIATE 12] and (4-cyanophenyl)methanesulfonyl chloride.

LC-MS (IE, m/z): 456 [M+1]⁺.

Example 17 A and B

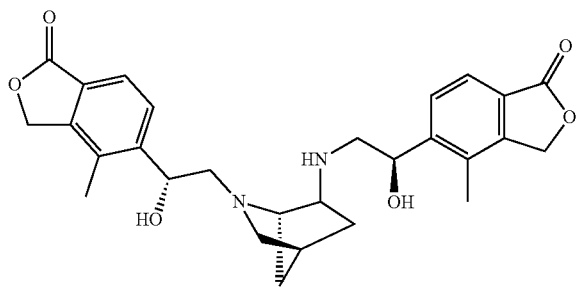 [SMILES: Cc1c([C@@H](O)CNC2C[C@H]3C[C@@H]2N(C[C@H](O)c2ccc4c(c2C)COC4=O)C3)ccc2c1COC2=O]

5-{(1R)-1-Hydroxy-2-[(1S,4S)-6-{[(2R)-2-hydroxy-2-(4-methyl-1-oxo-1,3-dihydro-2-benzofuran-5-yl)ethyl]amino}-2-azabicyclo[2.2.1]hept-2-yl]ethyl}-4-methyl-2-benzofuran-1(3H)-one 5-{(1R)-1-Hydroxy-2-[(1S,4S)-6-{[(2R)-2-hydroxy-2-(4-methyl-1-oxo-1,3-dihydro-2-benzofuran-5-yl)ethyl]amino}-2-azabicyclo[2.2.1]hept-2-yl]ethyl}-4-methyl-2-benzofuran-1(3H)-one was prepared in a similar fashion to that described for the synthesis of EXAMPLE 1 starting from 5-((1R)-2-((6S)-2-azabicyclo[2.2.1]heptan-6-ylamino)-1-hydroxyethyl)-4-methylisobenzofuran-1(3H)-one hydrochloride [INTERMEDIATE 13] and 4-methyl-5-[(2R)-oxiran-2-yl]-2-benzofuran-1(3H)-one [INTERMEDIATE 2B].

Faster eluting diastereomer: LC-MS (IE, m/z): 493 [M+1]$^+$.
Slower eluting diastereomer: LC-MS (IE, m/z): 493 [M+1]$^+$.

Example 18

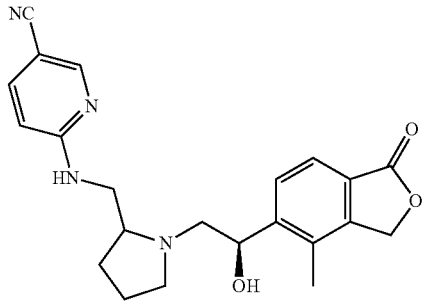 [SMILES: Cc1c([C@@H](O)CN2CCCC2CNc2ccc(C#N)cn2)ccc2c1COC2=O]

6-((1-(R)-2-Hydroxy-2-(4-methyl-1-oxo-1,3-dihydroisobenzofuran-5-yl)ethyl)pyrrolidin-2-yl)methylamino)nicotinonitrile A vial containing 5-[(1R)-2-[2-(aminomethyl)pyrrolidin-1-yl]-1-hydroxyethyl]-4-methyl-2-benzofuran-1(3H)-one hydrochloride [INTERMEDIATE 3] (0.067 g, 0.23 mmol) was treated with a solution of 6-chloropyridine-3-carbonitrile (0.035 g, 0.25 mmol) in DMF (0.5 mL) followed by diisopropylethylamine (0.105 mL, 0.60 mmol). The reaction mixture was shaken overnight at room temperature, and then concentrated in vacuo. The resulting residue was dissolved in DMSO (1 mL) and purified by HPLC to provide 5-[(1R)-2-[2-(aminomethyl)pyrrolidin-1-yl]-1-hydroxyethyl]-4-methyl-2-benzofuran-1(3H)-one hydrochloride and 6-chloropyridine-3-carbonitrile.

LC-MS (IE, m/z): 393 [M+1]$^+$.

Example 19

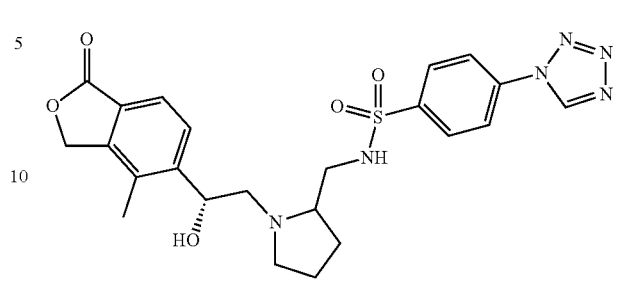

N-((1-((R)-2-Hydroxy-2-(4-methyl-1-oxo-1,3-dihydroisobenzofuran-5-yl)ethyl)pyrrolidin-2-yl)methyl)-4-(1H-tetrazol-1-yl)benzenesulfonamide N-((1-((R)-2-Hydroxy-2-(4-methyl-1-oxo-1,3-dihydroisobenzofuran-5-yl)ethyl)pyrrolidin-2-yl)methyl)-4-(1H-tetrazol-1-yl)benzenesulfonamide was prepared in a similar fashion to that described for the synthesis of EXAMPLE 13 starting from 5-41R)-2-(2-(aminomethyl)pyrrolidin-1-yl)-1-hydroxyethyl)-4-methylisobenzofuran-1(3H)-one hydrochloride [INTERMEDIATE 3] and commercially available 4-(1H-tetrazol-1-yl)benzene-1-sulfonyl chloride.

LC-MS (IE, m/z): 499 [M+1]$^+$.

Example 20

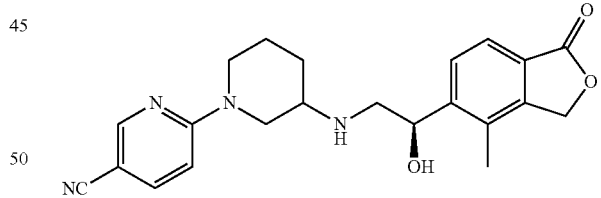

6-(3-((R)-2-Hydroxy-2-(4-methyl-1-oxo-1,3-dihydroisobenzofuran-5-yl)ethylamino)piperidin-1-yl)nicotinonitrile 6-(3-((R)-2-Hydroxy-2-(4-methyl-1-oxo-1,3-dihydroisobenzofuran-5-yl)ethylamino)piperidin-1-yl)nicotinonitrile was prepared in a similar fashion to that described for the synthesis of EXAMPLE 18 (this is still correct) starting from 541R)-1-hydroxy-2-(piperidin-3-ylamino)ethyl)-4-methylisobenzofuran-1(3H)-one hydrochloride [INTERMEDIATE 14] and 6-chloropyridine-3-carbonitrile.

LC-MS (IE, m/z): 393 [M+1]$^+$.

Example 21

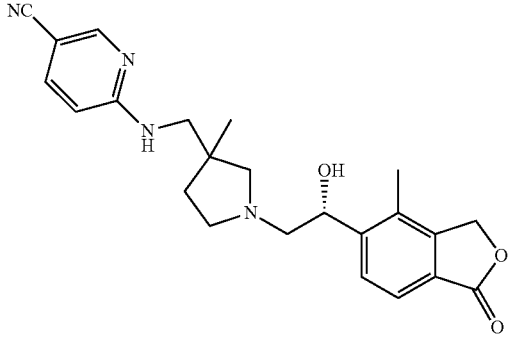 [SMILES: Cc1c([C@@H](O)CN2CCC(C)(CNc3ccc(C#N)cn3)C2)ccc2c1COC2=O]

6-((1-((R)-2-Hydroxy-2-(4-methyl-1-oxo-1,3-dihydroisobenzofuran-5-yl)ethyl)-3-methylpyrrolidin-3-yl)methylamino)nicotinonitrile 6-((1-((R)-2-Hydroxy-2-(4-methyl-1-oxo-1,3-dihydroisobenzofuran-5-yl)ethyl)-3-phenylpyrrolidin-3-yl)methylamino)nicotinonitrile was prepared in a similar fashion to that described for the synthesis of EXAMPLE 18 starting from 5-[(R)-2-[3-(Aminomethyl)-3-methylpyrrolidin-1-yl]-1-hydroxyethyl}-4-methyl-2-benzofuran-1(3H)-one hydrochloride [INTERMEDIATE 7] and 6-chloropyridine-3-carbonitrile.

LC-MS (IE, m/z): 407 [M+1]$^+$.

Example 22

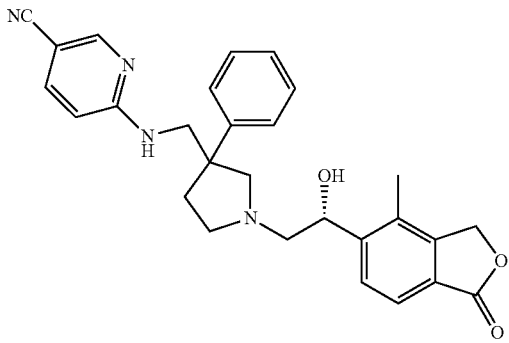 [SMILES: Cc1c([C@@H](O)CN2CCC(CNc3ccc(C#N)cn3)(c3ccccc3)C2)ccc2c1COC2=O]

6-((1-((R)-2-Hydroxy-2-(4-methyl-1-oxo-1,3-dihydroisobenzofuran-5-yl)ethyl)-3-phenylpyrrolidin-3-yl)methylamino)nicotinonitrile 6-((1-((R)-2-Hydroxy-2-(4-methyl-1-oxo-1,3-dihydroisobenzofuran-5-yl)ethyl)-3-methylpyrrolidin-3-yl)methylamino)nicotinonitrile was prepared in a similar fashion to that described for the synthesis of EXAMPLE 18 starting from 5-[(R)-2-[3-(Aminomethyl)-3-phenylpyrrolidin-1-yl]-1-hydroxyethyl}-4-methyl-2-benzofuran-1(3H)-one hydrochloride [INTERMEDIATE 15] and 6-chloropyridine-3-carbonitrile.

LC-MS (IE, m/z): 469 [M+1]$^+$.

Example 23

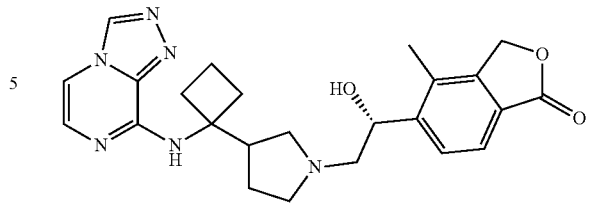

5-((1R)-2-(3-(1-([1,2,4]Triazolo[4,3-a]pyrazin-8-ylamino)cyclobutyl)pyrrolidin-1-yl)-1-hydroxyethyl)-4-methylisobenzofuran-1(3H)-one 5-((1R)-2-(3-(1-([1,2,4]Triazolo[4,3-a]pyrazin-8-ylamino)cyclobutyl)pyrrolidin-1-yl)-1-hydroxyethyl)-4-methylisobenzofuran-1(3H)-one was prepared in a similar fashion to that described for the synthesis of EXAMPLE 18 starting from 5-[(1R)-1-hydroxy-2-{[1-(pyrrolidin-3-yl)cyclobutyl]amino}ethyl]-4-methyl-2-benzofuran-1(3H)-one hydrochloride [INTERMEDIATE 5] and 8-chloro-[1,2,4]triazolo[4,3-a]pyrazine.

LC-MS (IE, m/z): 449 [M+1]$^+$.

Example 24

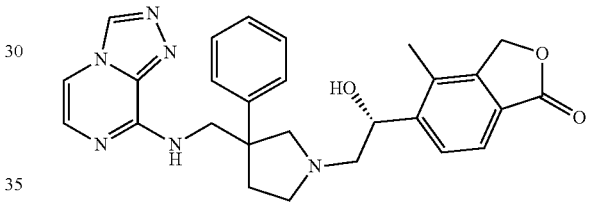

5-((1R)-2-(3-(((1,2,4]Triazolo[4,3-a]pyrazin-8-ylamino)methyl)-3-phenylpyrrolidin-1-yl)-1-hydroxyethyl)-4-methylisobenzofuran-1(3H)-one 5-((1R)-2-(3-(((1,2,4]Triazolo[4,3-a]pyrazin-8-ylamino)methyl)-3-phenylpyrrolidin-1-yl)-1-hydroxyethyl)-4-methylisobenzofuran-1(3H)-one was prepared in a similar fashion to that described for the synthesis of EXAMPLE 18 starting from 5-[(R)-2-[3-(Aminomethyl)-3-phenylpyrrolidin-1-yl]-1-hydroxyethyl}-4-methyl-2-benzofuran-1(3H)-one hydrochloride [INTERMEDIATE 15] and 8-chloro-[1,2,4]triazolo[4,3-a]pyrazine.

LC-MS (IE, m/z): 485 [M+1]$^+$.

Several assays may be used to measure functional inhibition of the ROMK channel by compounds of the instant invention. One assay that can be used is an electrophysiology assay that measures the electrical current that is generated as potassium permeates through the channel. Another ROMK functional assay makes use of the ability of thallium to permeate through open ROMK channels and increase the fluorescence of a dye previously loaded into the cells. Under control conditions, cells loaded with dye and exposed to thallium-containing medium display a time-dependent increase in fluorescence, the rate of which depends on number of functional channels. When cells are incubated in the presence of a channel inhibitor, the increase in fluorescence is attenuated in a concentration-dependent manner, and IC$_{50}$ values of inhibition by compounds can be accurately determined. This assay has been established with cell lines expressing either human, or rat ROMK channels, and operates in 384-well format.

Electrophysiology Assay

Block of Kir1.1 (ROMK1) currents was examined by whole cell voltage clamp (Hamill et. al. Pfluegers Archives 391:85-100 (1981)) using the IonWorks® Quattro automated electrophysiology platform (Molecular Devices, Sunnyvale, Calif.). Chinese hamster ovary cells stably expressing Kir1.1 channels were maintained in T-75 flasks in cell culture media in a humidified 10% $CO_2$ incubator at 37° C. Prior to an experiment, Kir1.1 expression was induced by overnight incubation with 1 mM sodium butyrate. On the day of the experiment, cells were dissociated with 2.5 ml of Versene™ (Invitrogen 15040-066) for approximately 6 minutes at 37° C. and suspended in 10 ml of bath solution containing (in mM): 150 NaCl, 10 KCl, 2.7 $CaCl_2$, 0.5 $MgCl_2$, 5 HEPES, pH 7.4. After centrifugation, the cell pellet was resuspended in approximately 4.0 ml of bath solution and placed in the IonWorks® instrument. The intracellular solution consisted of (in mM): 80 K gluconate, 40 KCl, 20 KF, 3.2 $MgCl_2$, 3 EGTA, 5 Hepes, pH 7.4. Electrical access to the cytoplasm was achieved by perforation in 0.13 mg/ml amphotericin B for 4 minutes. Amphotericin B (Sigma A-4888) was prepared as a 40 mg/ml solution in DMSO.

Voltage protocols and current recordings were performed using the IonWorks® HT software/hardware system. Currents were sampled at 1 kHz. No correction for liquid junction potentials was used. The test pulse, consisting of a 100 ms step to 0 mV from a holding potential of −70 mV, followed by a 100 ms voltage ramp from −70 mV to +70 mV, was applied before and after a 6 minutes compound incubation period. Test compounds were prepared by diluting DMSO stock solutions into the bath solution at 3× the final concentration and placed in the instrument in 96-well polypropylene plates. Current amplitudes were measured using the IonWorks® software. To assess compound potency, the fractional block during the voltage step to 0 mV was calculated in Microsoft® Excel (Microsoft, Redmond, Calif.), and dose-response curves were fitted with Igor Pro 4.0 (WaveMetrics, Lake Oswego, Oreg.). Normally, a control compound is included to support that the assay is giving consistent results compared to previous measurements, although the control is not required to obtain the results for the test compounds. The control was a compound of Formula I of the present invention, preferably with an $IC_{50}$ potency of less than 1 µM in this assay, or another compound (outside the scope of Formula I) that has an $IC_{50}$ potency in this assay of less than 1 µM.

Compounds of the Examples were tested in the electrophysiology assay and found to have a therapeutic level of potency.

Thallium Flux Assay

Cell Culture Conditions—

HEK293 cells stably expressing hROMK ($hK_{ir}1.1$) were grown at 37° C. in a 10% $CO_2$ humidified incubator in complete growth media: Dulbecco's Modified Eagle Medium supplemented with non-essential amino acids, Penicillin/Streptomycin/Glutamine, G418 and FBS. At >80% confluency, the media was aspirated from the flask and the sample was rinsed with 10 ml Calcium/Magnesium-free PBS. 5 ml of 1× trypsin (prepared in Ca/Mg Free PBS) was added to a T-225 flask and the flask was returned to 37° C./$CO_2$ incubator for 2-3 minutes. To dislodge the cell, the side of the flask was gently banged with a hand. The cells were triturated completely and then transferred to 25 ml complete media. The sample was then centrifuged at 1,500 rpm for 6 minutes, followed by resuspension in complete growth media and then cell concentration was determined. For typical re-seeding, 4E6 cells/T-225 flask were found to attain >80% confluency in 4 days. Under ideal growth conditions and appropriate tissue culture practices, this cell line is stable for 40-45 passages.

FluxOR Kit Components (Invitrogen F10017)
  FluxOR™ Reagent (Component A)
  FluxOR™ Assay Buffer (Component B)—10× Concentrate
  PowerLoad™ Concentrate (Component C)—100× Concentrate
  Probenecid (Component D) Lyophilized sample is kept at −20° C. Water soluble, 100× after solubilization in 1 ml water. Store at 4° C.
  FluxOR™ Chloride-free Buffer (Component E)—5× Concentrate
  Potassium sulfate ($K_2SO_4$) Concentrate (Component F)—125 mM in water. Store at 4° C.
  Thallium sulfate ($Tl_2SO_4$) Concentrate (Component G)—50 mM in water. Store at 4° C.
  DMSO (dimethyl sulfoxide, Component H) 1 ml (100%)

Reagent Preparation—

FluxOR Working Solutions
  1000× FluxOR™ Reagent: Reconstitute a vial of component A in 100 µl DMSO; Mix well; Store 10 µl aliquots at −20° C.
  1× FluxOR™ Assay Buffer: Dilute Component B 10-fold with water; Adjust pH to 7.4 with Hepes/NaOH; Filter and store at 4° C.
  Probenecid/Assay Buffer: 100 ml of 1× FluxOR™ Assay Buffer; 1 ml of reconstituted component D; Store at 4° C.
  Loading Buffer (per microplate): 10 µl 1000× FluxOR™ Reagent; 100 µl component C; 10 ml Probenecid/Assay Buffer
  Compound Buffer (per microplate): 20 ml Probenecid/Assay Buffer; 0.3 mM ouabain (10 mM ouabain in water can be stored in amber bottle/aluminum foil at room temperature); Test compound
  1× FluxOR™Chloride-Free Buffer: Prepare 1× working solution in water. Can be stored at room temperature
  Stimulant Buffer (prepared at 5× final concentration in 1× FluxOR™Chloride-Free Buffer): 7.5 mM Thallium sulfate and 0.75 mM Potassium sulfate (to give a final assay concentration of 3 mM Thallium 0.3 mM Potassium). Store at 4° C. when not in use. If kept sterile, this solution is good for months.

Assay Protocol—

The ROMK channel functional thallium flux assay is performed in 384 wells, using the FLIPR-Tetra instrument. HEK-hKir1.1 cells are seeded in Poly-D-Lysine microplates and kept in a 37° C.-10% $CO_2$ incubator overnight. On the day of the experiment, the growth media is replaced with the FluxOR™ reagent loading buffer and incubated, protected from light, at ambient temperature (23-25° C.) for 90 min. The loading buffer is replaced with assay buffer±test compound followed by 30 min incubation at ambient temperature, where the Thallium/Potassium stimulant is added to the microplate.

Step Protocol
1. Seed HEK-hKir1.1 cells (50 µl at 20,000 cells/well) in 384-well PDL coated Microplates 2. Allow cells to adhere overnight in humidified 37° C./10% CO$_2$ incubator
3. Completely remove cell growth media from microplate and replace with 25 μl loading buffer
4. Incubate Microplate at room temperature, protected form light, for 90 min
5. Remove loading buffer and replace with 25 μl 1× Assay Buffer±test compound.
6. Incubate microplate at room temperature, protected form light, for 30 min
7. At FLIPR-Tetra 384: Add stimulant (Thallium/Potassium) solution to microplate and monitor fluorescence. Excitation=400 nm, Emission=460 & 580 nm. Collect data for 10 min.

Data Calculation—

The fluorescence intensity of wells containing 3 μM of a standard control ROMK inhibitor of the present invention is used to define the ROMK-sensitive component of thallium flux. Fluorescence in the presence of test compounds is normalized to control values to provide % fluorescence change. IC$_{50}$ values represent the concentration of compound that inhibits 50% of the ROMK thallium flux signal.

Assay Standard—

Normally, a control compound is included to support that the assay is giving consistent results compared to previous measurements, although the control is not required to obtain the results for the test compounds. The control can be a compound of Formula I of the present invention, preferably with an IC$_{50}$ potency of less than 1 μM in this assay. Alternatively, the control could be another compound (outside the scope of Formula I) that has an IC$_{50}$ potency in this assay of less than 1 μM.

Representative examples of data collected for compounds of the present invention using the Electrophysiology and Thallium Flux Assays are shown in Table 1 below.

TABLE 1

| EXAMPLE | Thallium Flux Assay IC$_{50}$ (μM) | EP Assay IC$_{50}$ (μM) |
|---------|-----|-----|
| 1 | 0.414 | 0.595 |
| 2 | 0.172 | 0.42 |
| 3 | 0.176 | 0.51 |
| 4 | 0.5235 | 0.278 |
| 5 | 0.082 | |
| 6 | 0.143 | 0.446 |
| 7 | 0.277 | |
| 8 | 0.847 | |
| 9A | 0.188 | 0.321 |
| 9B | 0.29 | 0.254 |
| 10 | 0.504 | 2.058 |
| 11 | 0.648 | |
| 12 | 0.542 | 1.369 |
| 13 | 0.162 | 0.269 |
| 14 | 0.122 | 0.15 |
| 15 | 0.639 | 1.389 |
| 16 | 1.037 | |
| 17A | 0.5 | 1.42 |
| 17B | 0.581 | |
| 18 | 0.534 | 0.065 |
| 19 | 0.2062 | 0.245 |
| 20 | 0.2653 | 0.052 |
| 21 | 0.5473 | 0.103 |
| 22 | 0.8077 | 0.34 |
| 23 | 0.4006 | |
| 24 | 0.8931 | |

While the invention has been described with reference to certain particular embodiments thereof, numerous alternative embodiments will be apparent to those skilled in the art from the teachings described herein. Recitation or depiction of a specific compound in the claims (i.e., a species) without a specific stereoconfiguration designation, or with such a designation for less than all chiral centers, is intended to encompass the racemate, racemic mixtures, each individual enantiomer, a diastereoisomeric mixture and each individual diastereomer of the compound where such forms are possible due to the presence of one or more asymmetric centers. All patents, patent applications and publications cited herein are incorporated by reference in their entirety.

What is claimed is:
1. A compound having structural Formula I:

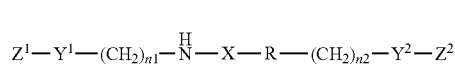

or a pharmaceutically acceptable salt thereof wherein:
—X—R—(CH$_2$)n2- is

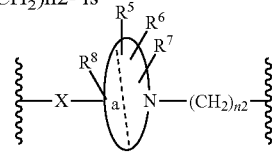

and where R is

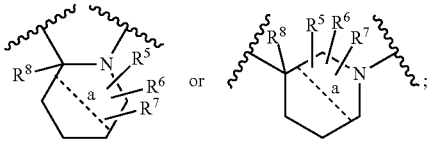

a is —CH$_2$—, —CH$_2$CH$_2$—, —CH$_2$CH$_2$CH$_2$—, —CH$_2$OCH$_2$— or absent; wherein the —CH$_2$— is optionally substituted with 1-2 of —F, and wherein the —CH$_2$CH$_2$—, —CH$_2$CH$_2$CH$_2$—, or —CH$_2$OCH$_2$— is optionally substituted with 1-3 of —F; and wherein a forms a bridge between two non-adjacent carbons;

R$^5$ is —H, —F with the proviso that —F is not attached to a carbon also bonded to nitrogen, —CH$_3$, —CF$_3$, —CHF$_2$, —CHF$_2$, or —CH$_2$OH, or R$^5$ represents di-substitution on a single carbon with two of —F with the proviso that the two —F are not attached to a carbon also bonded to nitrogen, or two of —CH$_3$;

R$^6$ and R$^7$ are individually either —H, —C$_{1-3}$ alkyl optionally substituted with 1-3 of —F, or R$^6$ and R$^7$ can be taken together with the carbon atom to which they are attached to form C$_{4-3}$ cycloalkyl optionally substituted with 1-3 of —F;

R$^8$ is —H, —F, —CH$_3$, —CF$_3$, —CHF$_2$, —CH$_2$F, or —CH$_2$OH, or phenyl optionally substituted with 1-3 of —F or —C$_{1-3}$ alkyl;

n1 and n2 can be individually either 0 or 1;

Z$^1$ is:

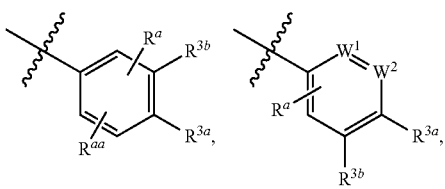

-continued

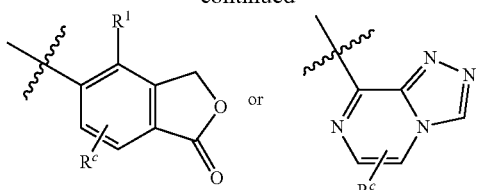

$Z^2$ is:

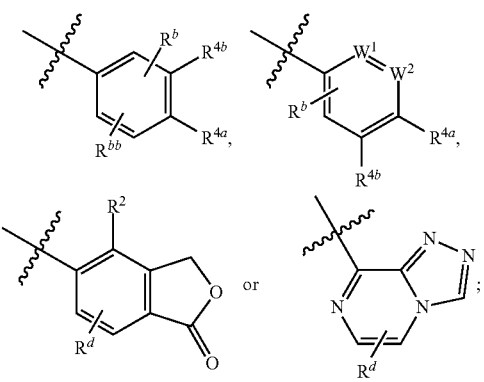

one of $W^1$ and $W^2$ is N and the other is CH;

$R^1$ and $R^2$ are each independently —H, —F, —Cl, —Br, cyclopropyl, —$C_{1-3}$alkyl optionally substituted with 1-3 of —F, or —$OC_{1-3}$alkyl optionally substituted with 1-3 of —F;

one of $R^{3a}$ and $R^{3b}$ is —CN, tetrazolyl, or —S(O)$_2C_{1-3}$ alkyl and the other is —H, —F, —Cl, —Br, —S—CH$_3$, —NH—CH$_3$, —O-cyclopropyl, —$C_{1-3}$alkyl optionally substituted with 1-3 of —F, or —$OC_{1-3}$ alkyl optionally substituted with 1-3 of —F;

one of $R^{4a}$ and $R^{4b}$ is —CN, tetrazolyl, or —S(O)$_2C_{1-3}$ alkyl and the other is —H, —F, —Cl, —Br, —S—CH$_3$, —NH—CH$_3$, —O-cyclopropyl, —$C_{1-3}$alkyl optionally substituted with 1-3 of —F, or —$OC_{1-3}$ alkyl optionally substituted with 1-3 of —F;

$R^a$, $R^{aa}$, $R^b$ and $R^{bb}$ are each independently —H, —F, —Cl, —$C_{1-3}$alkyl optionally substituted with 1 to 3 of —F, or —$OC_{1-3}$alkyl optionally substituted with 1 to 3 of —F;

$R^c$ and $R^d$ are each independently —H, —F, —Cl, —$C_{1-3}$ alkyl optionally substituted with 1 to 3 of —F, or —$OC_{1-3}$ alkyl optionally substituted with 1 to 3 of —F;

X is absent or $C_1$ alkyl having 2 substituents independently —H, or —$C_{1-3}$alkyl optionally substituted with 1 to 3 of —F, wherein two —$C_{1-3}$alkyl substituents can be taken together with the $C_1$ alkyl to which they are attached to form a —$C_{3-6}$cycloalkyl; and one of $Y^1$ or $Y^2$ is —CH(OH)—; and the other is —CH (OH)—; —S(O)$_2$—; —S(O)$_2$CH$_2$—; —CH$_2$— wherein —CH$_2$— is optionally substituted with —$C_{1-3}$alkyl optionally substituted with —OH, —$OC_{1-3}$alkyl, or -1-3 of —F, or absent; provided that where $Y^1$ or $Y^2$ is —S(O)$_2$— or —S(O)$_2$CH$_2$—, then the adjacent n1 or n2, respectively, is 0; and provided further that where $Y^1$ or $Y^2$ is —CH(OH)—, then the adjacent n1 or n2, respectively, is 1.

2. The compound of claim 1 wherein R is:

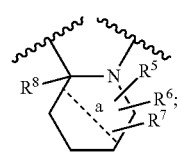

R-IV or a pharmaceutically acceptable salts thereof.

3. The compound of claim 1 wherein R is:

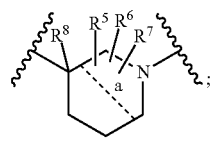

R-V or a pharmaceutically acceptable salts thereof.

4. The compound of claim 1 wherein:

$Z^1$ is

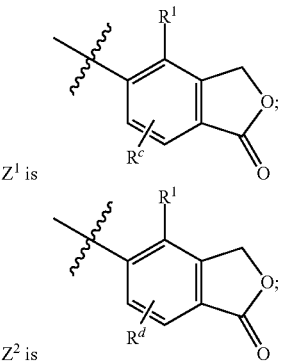

$Z^2$ is or a pharmaceutically acceptable salts thereof.

5. The compound of claim 1 wherein:

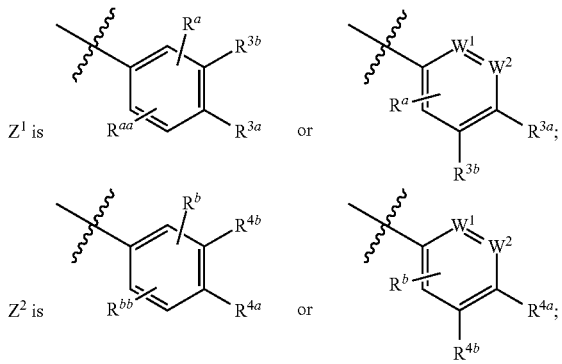

$Z^1$ is $Z^2$ is or a pharmaceutically acceptable salts thereof.

6. The compound of claim 1 wherein:

one of $R^{3a}$ and $R^{3b}$ is —CN or tetrazolyl and the other is —H, —F, —Cl, —Br, —$C_{1-3}$alkyl optionally substituted with 1-3 of —F, or —$OC_{1-3}$alkyl optionally substituted with 1-3 of —F; and/or one of $R^{4a}$ and $R^{4b}$ is —CN or tetrazolyl and the other is —H, —F, —Cl, —Br, —$C_{1-3}$alkyl optionally substituted with 1-3 of —F, or —$OC_{1-3}$alkyl optionally substituted with 1-3 of —F;

or a pharmaceutically acceptable salts thereof.

7. The compound of claim 1 wherein a is —CH$_2$— or absent or a pharmaceutically acceptable salt thereof.

8. The compound of claim 1 wherein a is absent or a pharmaceutically acceptable salt thereof.

9. compound selected from:

5-{(1R)-1-Hydroxy-2-[2-({[(2R)-2-hydroxy-2-(4-methyl-1-oxo-1,3-dihydro-2-benzofuran-5-yl)ethyl]amino}methyl)piperidin-1-yl]ethyl}-4-methyl-2-benzofuran-1(3H)-one;

5-{(1R)-1-Hydroxy-2-[2-({[2-hydroxy-1-(4-methyl-1-oxo-1,3-dihydro-2-benzofuran-5-yl)ethyl]amino}methyl)piperidin-1-yl]ethyl}-4-methyl-2-benzofuran-1(3H)-one;

5-{(1R)-1-Hydroxy-2-[3-({[(2R)-2-hydroxy-2-(4-methyl-1-oxo-1,3-dihydro-2-benzofuran-5-yl)ethyl]amino}methyl)-3-methylpiperidin-1-yl]ethyl}-4-methyl-2-benzofuran-1(3H)-one;

6-{1-Hydroxy-2-[({1-[(2R)-2-hydroxy-2-(4-methyl-1-oxo-1,3-dihydro-2-benzofuran-5-yl)ethyl]piperidin-2-yl}methyl)amino]ethyl}pyridine-3-carbonitrile;

5-{(1R)-1-Hydroxy-2-[(1S,4S)-6-{[(2R)-2-hydroxy-2-(4-methyl-1-oxo-1,3-dihydro-2-benzofuran-5-yl)ethyl]amino}-2-azabicyclo[2.2.1]hept-2-yl]ethyl}-4-methyl-2-benzofuran-1(3H)-one;

6-(3-((R)-2-Hydroxy-2-(4-methyl-1-oxo-1,3-dihydroisobenzofuran-5-yl)ethylamino)piperidin-1-yl)nicotinonitrile;

or a pharmaceutically acceptable salt thereof.

10. A pharmaceutical composition comprised of a compound of claim 1 or a pharmaceutically acceptable salt thereof and a pharmaceutically acceptable carrier.

* * * * *